(12) United States Patent
Dimitrakakis et al.

(10) Patent No.: US 12,376,930 B1
(45) Date of Patent: *Aug. 5, 2025

(54) HANDHELD SURGICAL SYSTEMS WITH INTERCHANGEABLE DEXTEROUS END-EFFECTORS

(71) Applicant: Panda Surgical Limited, London (GB)

(72) Inventors: Emmanouil Dimitrakakis, London (GB); Keshav Iyengar, London (GB); George Dwyer, London (GB); Dimitrios Psychogyios, London (GB)

(73) Assignee: Panda Surgical Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/952,944

(22) Filed: Nov. 19, 2024

Related U.S. Application Data

(63) Continuation of application No. 18/792,533, filed on Aug. 1, 2024, now Pat. No. 12,150,729.
(Continued)

(30) Foreign Application Priority Data

Feb. 2, 2024 (EP) ..................... 24386010

(51) Int. Cl.
*A61B 34/00* (2016.01)
*A61B 17/29* (2006.01)
(Continued)

(52) U.S. Cl.
CPC .......... *A61B 34/71* (2016.02); *A61B 17/2909* (2013.01); *A61B 34/37* (2016.02);
(Continued)

(58) Field of Classification Search
CPC ......... A61B 17/00; A61B 17/28; A61B 17/29; A61B 17/2909; A61B 2017/0046; A61B 34/00; A61B 34/37; A61B 34/71
See application file for complete search history.

(56) References Cited

U.S. PATENT DOCUMENTS

| 7,169,141 B2 | 1/2007 | Brock et al. |
| 7,828,808 B2 | 11/2010 | Hinman et al. |

(Continued)

FOREIGN PATENT DOCUMENTS

| CA | 2271811 A1 | 11/1999 |
| CA | 2920822 A1 | 3/2015 |

(Continued)

OTHER PUBLICATIONS

Anderson et al., "Robot-like dexterity without computers and motors: a review of hand-held laparoscopic instruments with wrist-like tip articulation," Expert Review of Medical Devices, vol. 13(7):661-672 (Jan. 2016).

(Continued)

*Primary Examiner* — Vi X Nguyen
(74) *Attorney, Agent, or Firm* — Greenberg Traurig, LLP; Christopher C. Bolten; Albert K. Heng

(57) ABSTRACT

Handheld surgical systems having an adjustable, ergonomic handheld controller and a series of interchangeable surgical instruments with dexterous, end-effectors for performing a surgical procedure, e.g., removing brain tumor tissue from confined spaces, and methods of use thereof are disclosed. The end-effector may be actuated in one or more degrees of freedom via a tendon routing system comprising a plurality of antagonistic pairs of tendons extending from the end-effector to a plurality of independently rotatable capstan shafts disposed within a housing of the interchangeable instrument and configured to be releasably and operatively coupled to one or more motors disposed within the handheld controller.

30 Claims, 24 Drawing Sheets

Related U.S. Application Data

(60) Provisional application No. 63/570,158, filed on Mar. 26, 2024.

(51) Int. Cl.
*A61B 34/37* (2016.01)
*A61B 17/00* (2006.01)
*A61B 90/00* (2016.01)

(52) U.S. Cl.
CPC .......... *A61B 2017/00398* (2013.01); *A61B 2017/00424* (2013.01); *A61B 2017/00464* (2013.01); *A61B 2017/2903* (2013.01); *A61B 2017/2927* (2013.01); *A61B 2017/2946* (2013.01); *A61B 2034/742* (2016.02); *A61B 2090/067* (2016.02)

(56) References Cited

U.S. PATENT DOCUMENTS

| | | |
|---|---|---|
| 7,922,739 B2 | 4/2011 | Downey |
| 8,267,958 B2 | 9/2012 | Braun |
| 8,623,027 B2 | 1/2014 | Price et al. |
| 8,821,480 B2 | 9/2014 | Burbank |
| 8,845,622 B2 | 9/2014 | Paik et al. |
| 8,998,799 B2 | 4/2015 | Orban, III et al. |
| 9,320,568 B2 | 4/2016 | Orban, III et al. |
| 9,486,236 B2 | 11/2016 | Price et al. |
| 9,597,104 B2 | 3/2017 | Nicholas et al. |
| 9,655,601 B2 | 5/2017 | Young et al. |
| 9,706,981 B2 | 7/2017 | Nicholas et al. |
| 9,724,163 B2 | 8/2017 | Orban |
| D798,449 S | 9/2017 | Canady et al. |
| 9,868,198 B2 | 1/2018 | Nicholas et al. |
| 9,993,258 B2 | 6/2018 | Shelton, IV et al. |
| 10,226,254 B2 | 3/2019 | Cabrera et al. |
| 10,357,317 B2 | 7/2019 | Dupont et al. |
| 10,575,888 B2 | 3/2020 | Coillard-Lavirotte et al. |
| 10,828,059 B2 | 11/2020 | Price et al. |
| 11,020,197 B2 | 6/2021 | Sholev |
| 11,116,594 B2 | 9/2021 | Beardsley |
| 11,172,929 B2 | 11/2021 | Shelton, IV |
| 11,224,487 B2 | 1/2022 | Canady et al. |
| 11,246,615 B2 | 2/2022 | Lee et al. |
| 11,357,585 B2 | 6/2022 | Simi et al. |
| 11,484,379 B2 | 11/2022 | Sutherland et al. |
| 12,150,729 B1 * | 11/2024 | Dimitrakakis ......... A61B 34/37 |
| 12,257,015 B1 | 3/2025 | Iyengar et al. |
| 2006/0058825 A1 | 3/2006 | Ogura et al. |
| 2006/0201130 A1 | 9/2006 | Danitz |
| 2007/0221700 A1 | 9/2007 | Ortiz et al. |
| 2008/0196533 A1 | 8/2008 | Bergamasco et al. |
| 2008/0208195 A1 | 8/2008 | Shores et al. |
| 2008/0262654 A1 | 10/2008 | Omori et al. |
| 2011/0144656 A1 | 6/2011 | Lee et al. |
| 2011/0174099 A1 * | 7/2011 | Ross ............... A61B 17/00 74/89.32 |
| 2012/0089131 A1 * | 4/2012 | Zemlok ............ A61B 17/115 606/1 |
| 2012/0104071 A1 | 5/2012 | Bryant |
| 2015/0157321 A1 | 6/2015 | Zergiebel et al. |
| 2017/0245856 A1 | 8/2017 | Baxter, III et al. |
| 2017/0311945 A1 | 11/2017 | Timm et al. |
| 2017/0319200 A1 | 11/2017 | Nicholas |
| 2018/0161109 A1 | 6/2018 | Overmyer et al. |
| 2018/0325609 A1 | 11/2018 | Kostrzewski et al. |
| 2019/0090963 A1 | 3/2019 | Canady et al. |
| 2019/0159850 A1 | 5/2019 | Seow |
| 2019/0298400 A1 | 10/2019 | Horeman |
| 2020/0015836 A1 | 1/2020 | Nicholas et al. |
| 2020/0061796 A1 | 2/2020 | Jore et al. |
| 2020/0113557 A1 | 4/2020 | Sholev et al. |
| 2020/0222136 A1 | 7/2020 | Abrahams et al. |
| 2020/0405403 A1 | 12/2020 | Shelton, IV et al. |
| 2021/0196413 A1 | 7/2021 | Inoue |
| 2022/0022977 A1 * | 1/2022 | Beckman ............ B25J 5/02 |
| 2023/0068155 A1 | 3/2023 | Stoyanov et al. |

FOREIGN PATENT DOCUMENTS

| | | |
|---|---|---|
| CN | 109171837 A | 1/2019 |
| EP | 1915967 B1 | 3/2010 |
| EP | 2233081 B1 | 3/2015 |
| GB | 2509523 A | 7/2014 |
| WO | WO-2010112608 A1 | 10/2010 |
| WO | WO-2015142788 A1 | 9/2015 |
| WO | WO-2019228169 A1 | 12/2019 |
| WO | WO-2021165647 A1 | 8/2021 |
| WO | WO-2021225863 A1 | 11/2021 |

OTHER PUBLICATIONS

Awtar et al., "FlexDex™: A Minimally Invasive Surgical Tool With Enhanced Dexterity and Intuitive Control," Journal of Medical Devices, vol. 4:035003-1-035003-8, (Sep. 2010).

Battenberg et al., "A novel handheld robotic-assisted system for unicompartmental knee arthroplasty: surgical technique and early survivorship," Journal of Robotic Surgery, vol. 14:55-60 (2020).

Bensignor et al., "Evaluation of the effect of a laparoscopic robotized needle holder on ergonomics and skills," Surg Endosc., vol. 30:446-454, (2016).

Boiadjiev et al., "Handheld Robotized Systems for Orthopedic Surgery," MMS vol. 67:112-120 (2019).

Burgner et al., "A bimanual teleoperated system for endonasal skull base surgery." In: 2011 IEEE/RSJ International Conference on Intelligent Robots and Systems, IEEE, pp. 2517-2523, (Sep. 2011).

Burgner et al., "A Bimanual Teleoperated System for Endonasal Skull Based Surgery." International Conference on Intelligent Robots and Systems, pp. 2517-2523 (2011).

Chitalia et al., "Design and Kinematics Analysis of a Robotic Pediatric Neuroendoscope Tool Body," IEEE/ASME Transactions on Mechatronics, vol. 25(2):985-995, (Apr. 2020).

Coemert et al., "A handheld flexible manipulator system for frontal sinus surgery," Int J Computer Assisted Radiology and Surgery, pp. 1-11, (Jun. 2020).

Culmone et al., "A Fully 3D-Printed Steerable Instrument for Minimally Invasive Surgery," Materials, vol. 14:7910, pp. 1-18, (Dec. 2021).

Dimitrakakis, et al., "A Novel Handheld Robotic System for Endoscopic Neurosurgery: A Cadaver Pilot Study." The Hamlyn Symposium on Medical Robotics, pp. 1-3, (Jun. 2023).

Dimitrakakis, et al., "A spherical joint robotic end-effector for the expanded endoscopic endonasal approach," Journal of Medical Robotics Research, 5(03n04), pp. 1-13, (2020).

Dimitrakakis, et al., "An intuitive surgical handle design for robotic neurosurgery," Int'l Journal of Computer Assisted Radiology and Surgery, pp. 1-9, (May 2021).

Dimitrakakis et al., "Handheld robotic device for endoscopic neurosurgery: system integration and pre-clinical evaluation," Frontiers in Robotics and AI, vol. 11:1400017, pp. 1-16 (Jun. 2024).

Dimitrakakis, et al., "Robotic Handle Prototypes for Endoscopic Endonasal Skull Base Surgery: Pre-clinical Randomised Controlled Trial of Performance and Ergonomics," Annals of Biomedical Engineering, vol. 50(5):549-563, (May 2022).

Done et al., "How should trackball directional movement intuitively relate to as end effector?" Proceedings of the Human Factor and Ergonomics Society 47th Annual Meeting, pp. 1122-1125, (2003).

Eastwood et al., "A Steerable Neuroendoscopic Instrument Using Compliant Contact-Aided Joints and Monolithic Articulation," Journal of Medical Devices, vol. 14:025002-1-025002-15 (Jun. 2020).

Ebrahimi et al., "Hand-Held Steerable needle Device," MICCAI, LNCS, vol. 2879:223-230, (2003).

Extended European Search Report for European Application No. 20200386011, dated Jul. 21, 2020, 21 pages.

Feng et al., "Handheld laparoscopic robotized instrument: progress or challenge," Surgical Endoscopy, vol. 34:719-727, (2020).

(56) References Cited

OTHER PUBLICATIONS

Feng et al., "Handheld robotic needle holder training: slower but better," Surgical Endoscopy, vol. 35:1667-1674, (2021).
Focacci et al., "Lightweight Hand-Held Robot for Laparoscopic Surgery," IEEE Int'l Conference on Robotics and Automation, WeB8.1, pp. 599-604, (Apr. 2007).
Girerd et al., "Design and Control of a Hand-Held Concentric Tube Robot for Minimally Invasive Surgery," IEEE Transactions on Robotics, vol. 37(4):1022-1038, (Aug. 2021).
Hackethal et al., "Handheld articulating laparoscopic instrument driven by robotic technology. First clinical experience in gynecological surgery," Gynecol Surg., vol. 9:203-206, (2012).
Han et al., "Ergonomic Design Process of Minimally Invasive Surgery Instrument hand-held manipulator with kinematic, psychologic analysis," 16th International Conference on Ubiquitous Robert (UR), pp. 306-312, (Jun. 2019).
Hardon et al., "A new modular mechanism that follows full detachability and cleaning of steerable laparoscopic instruments," Surgical Endoscopy, pp. 1-10 (May 2019).
Hardon et al., "Safe implementation of hand-held steerable laparoscopic instruments: as survey among EAES surgeons," Updates in Surgery, pp. 1-6, (Feb. 2022).
Hassan-Zahraee, et al., "Mechatronic Design of a Hand-Held Instrument with Active Trocar for Laparoscopy," IEEE Int'l Conference on Robotics and Automation, pp. 1890-1895, (May 2011).
Hernandez-Valderrama et al., "Steerable Surgical Instrument for Conventional and Single-Site Minimally Invasive Surgery," Surgical Innovation, vol. 29(3):449-458, (2022).
Hessinger et al., "Handheld Surgical Drill With Integrated Thrust Force Recognition," The 4th IEEE Int'l Conference on E-Health and Bioengineering—EHB, pp. 1-4, (Nov. 2013).
Hung et al., "Handle Navigation for a Smart Handheld Robot," EPiC Series in Health Science, vol. 3:181-183, (2019).
International Search Report & Written Opinion For International Application No. PCT/GB2021/050316, dated Apr. 19, 2021, 10 Pages.
Jelinek et al., "Design for Additive Manufacturer of Fine Medical Instrumentation—DragonFlex Case Study," Journal of Mechanical Design, vol. 137:111416-1-111416-7, (Nov. 2015).
Jinno, M., "Proof of concept for a wrist mechanism for articulated forceps for use in robot-assisted laparoscopic surgery," Jinno Robomech J., vol. 5(5): pp. 1-9 (2018).
Kawamata et al., "Novel flexible forceps for endoscopic transsphenoidal resection of pituitary tumors: technical report," Neurosurg Rev., vol. 31:65-68, (2008).
Kawashima et al., "Robots in laparoscopic surgery: current and future status," BMC Biomedical Engineering, vol. 1(12):1-6, (2019).
Kotev et al., "Design of a Hand-Held Robotized Module for Bone Drilling and Cutting in Orthopedic Surgery," IEEE/SICE Int'l Symposium on System Integration (SII), pp. 504-509, (Dec. 2012).
Kumar et al., "Design, Analysis and Experimental Validation of a Novel 7-Degrees of Freedom Instrument for Laparoscopic Surgeries," Annal of Biomedical Engineering, pp. 1-20, Sep. 2022).
Legrand et al., "A miniature robotic steerable endoscope for maxillary sinus surgery called PliENT," Scientific Reports, vol. 12:2299, pp. 1-15 (2022).
Leite et al., "Assessment of Laparoscopic Skills Performance: 2D Versus 3D Vision and Classic Instrument Versus New Hand-Held Robotic Device for Laparoscopy," Surgical Innovation, vol. 23(1):52-61, (2016).
Li et al., "Application of Three-Dimensional (3D) Printing in Neurosurgery," Advances in Materials Science and Engineering, vol. 2022:ID 80156252022; pp. 1-13, (Sep. 2022).
Lonner, J.S., MD "Robotically Assisted Unicompartmental Knee Arthroplasty with a Handheld Image-Free Sculpting Tool," Operative Techniques in Orthopaedics, 25:104-113, (2015).
Ma et al., "An Active Steering Hand-Held Robotic System for Minimally Invasive Orthopaedical Surgery Using a Continuum Manipulator," IEEE Robotics and Automation Letters, vol. 6(2):1622-1629 (Apr. 2021).
Mallmann et al., "The Lamb's Head as a Model for Surgical Skills Development in Endonasal Surgery," Journal of Neurological Surgery Part B: Skull Base, vol. 77:466-472, (Mar. 2016).
Mao et al., "Anatomical and Technical Considerations of Robot-Assisted Cervical Pedicle Screw Placement: A Cadaveric Study," Global Spine Journal, vol. 13(7):1992-2000, (2023).
Miyazaki et al., "A master-Slave Integrated Surgical Robot With Active Motion Transformation Using Wrist Axis," IEEE/ASME Transactions on Mechatronics, vol. 23(3):1215-1225, (Jun. 2018).
Miyazaki et al., "Pneumatically Driven Handheld Forceps with Force Display Operated by Motion Sensor," IEEE Int'l Conference on Robotics and Automation (ICRA), pp. 604-609, (May 2015).
Mladina et al., "The Validity of Training Endoscopic Sinus and Skull Base Surgery Techniques on the Experimental Head Model," Journal of Craniofacial Surgery, vol. 29(2):498-501, (2017).
Mladina et al., "Training Cerebrospinal Fluid Leak Repair with Nasoseptal Flap on the Lamb's Head," ORL, 75(1):32-36, (Jan. 2013).
Okazawa et al., "Hand-Held Steerable Needle Device," IEEE/ASME Transactions on Mechatronics, vol. 10(3):285-296, (Jun. 2002).
Osawa et al., "2.5-mm articulated endoluminal forceps using a compliant mechanism," International Journal of Computer Assisted Radiology and Surgery, pp. 1-8 (Jul. 2022).
Payne et al., "A Hand-Held Flexible Mechatronic Device for Arthroscopy," IEEE/RSJ Int'l Conference on Intelligent Robots and Systems (IROS), pp. 817-823, (Sep. 2015).
Pereira et al., "Hand-Held Robotic Device for Laparoscopic Surgery and Training," IEEE Xplore, pp. 1-8, (Jul. 2024).
Piccigallo, et al., "Hand-Held robotic instrument for dextrous laparoscopic interventions," Int J Med Robotics Comput Assis Surg., vol. 4:331-338, (Jul. 2008).
Ravina et al., "Conical drill bit for optimized external ventricular drain placement: a proof-of-concept study," J Neurosurg, vol. 139:881-891 (Sep. 2023).
Riojas et al., "A Hand-Held Non-Robotic Surgical Tool With A Wrist and an Elbow," IEEE Transactions on Biomedical Engineering, vol. 66(11):3176-3184, (Nov. 2019).
Rox et al., "An Experimental Comparison of Two Two User Interface Designs for a Hand-Held Surgical Robot," Proceedings of the 2017 Design of Medical Devices Conference, DMD2017, pp. 1-2 (Apr. 2017).
Sanchez-Margallo et al., "Assessment of Postural Ergonomics and Surgical Performance in Laparoendoscopic Single-Site Surgery Using a Handheld Robotic Device," Medical Technology, Innovation, and Invention, vol. 25(3):208-217, (2018).
Sanchez-Margallo et al., "Initial experience using a robotic-driver laparoscopic needle holder with ergonomic handle: assessment of surgeons' task performance and ergonomics," Int J Cars, vol. 12:2069-2077, (Jun. 2017).
Sanicibrian et al., "Design and evaluation of a new ergonomic handle for instruments in minimally invasive surgery," Journal of Surgical Research, vol. 188:88-99, (2014).
Santona et al., "Training models and simulators for endoscopic transsphenoidal surgery: a systematic review," Neurosurgical Review, vol. 46(1):248, pp. 1-16, (Sep. 2023).
Schild et al., "Evaluation of a curved surgical prototype in a human larynx," European Archives of Ot-Rhino-Laryngology, pp. 1-10, (Mar. 2021).
Skitarelic et al., "Lamb's head: The model for novice education in endoscopic sinus surgery," World Journal of Methodology, vol. 5(3):144-148, (Sep. 2015).
Starup-Hansen et al., "A Handheld Robot for Endoscopic Endonasal Skull Base Surgery: Updated Preclinical Validation Study (Ideal Stage 0)," J Neurol Surg—Part B, pp. 1-8, (Apr. 2024).
Troccaz et al., "Frontiers of Medical Robotics: From Concept to Systems to Clinical Translations," Annual Review, vol. 16(51):193-218, (Mar. 2019).
US Food & Drug Admiration Letter Dated Mar. 20, 2018 RE: HX Device.

(56) References Cited

OTHER PUBLICATIONS

Uysal et al., "Evaluation of new motorized articulating laparoscopic instruments by laparoscopic novices using a standardized laparoscopic skills curriculum," Surgical Endoscopy, vol. 35:979-988, (2021).
Wang et al., "A Handheld Steerable Surgical Drill With a Novel Miniaturized Articulated Joint Module for Dexterous Confined-Space Bone Work," IEEE Transactions on Biomedical Engineering, vol. 69(9):2926-2638, (Sep. 2022).
Wu et al., "Robotic Electrospinning Actuated by Non-Circular Joint Continuum Manipulator for Endoluminal Therapy," IEEE, pp. 1-7, (2021).
Yamashita et al., "Handheld Laparoscopic Forceps Manipulator Using Multi-slider Linkage Mechanisms," MICCAI—LNCS, vol. 3217:121-128, (2004).
Yang, et al., "Design and Evaluation of a Dexterous and Modular Hand-Held Surgical Robot for Minimally Invasive Surgery," Journal of Medical Devices, vol. 13 041005-1-041005-10, (Dec. 2019).
Yang et al., "Design and implementation of a hand-held robot-assisted minimally invasive surgical device with enhanced intuitive manipulability and stable grip force," Int Journal of Medical Robotics and Computer Assisted Surgery, pp. 1-11, (Feb. 2021).
Zahraee et al., "Robotic Hand-Held Surgical Device: Evaluation of End-Effector's Kinematics and Development of Proof-of-Concept Prototypes," MICCAI—Part III LNCS, vol. 6363:432-439 (2010).
Zahraee, et al., "Toward the Development of a hand-Held Surgical Robot for Laparoscopy," IEEE/ASME Transactions on Mechatronics, vol. 15(6):853-861, (Dec. 2010).
Zdichavsky et al., "Single-port live donor nephrectomy using a novel Curved Radius R2 Surgical System in an in vivo model," Minimally Invasive Therapy & Allied Technologies, vol. 24(2):63-67 (2015).
Invitation to Pay Additional Fees and Partial Search Report dated May 15, 2025 in Int'l PCT Patent Appl. Serial No. PCT/IB2025/051039.

\* cited by examiner

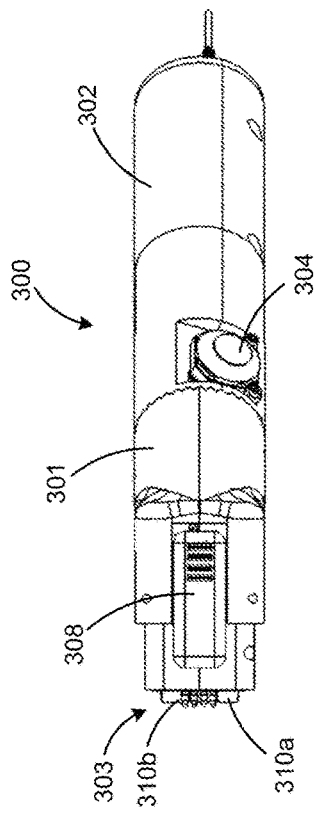
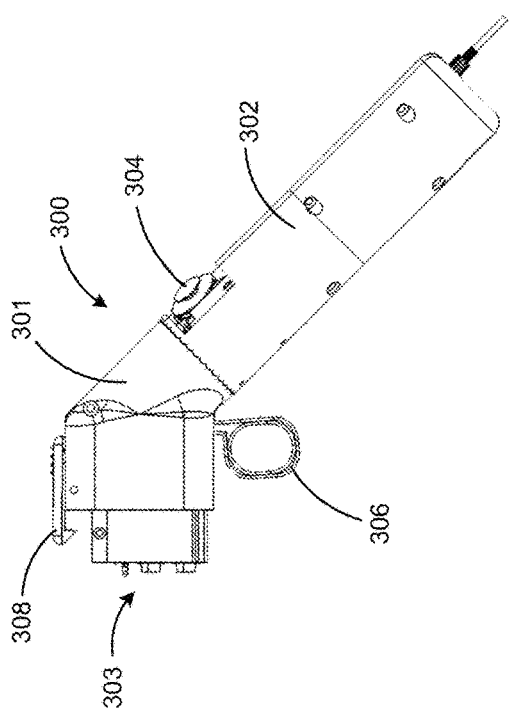
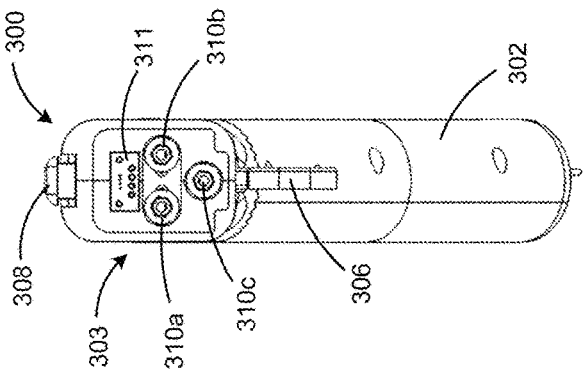
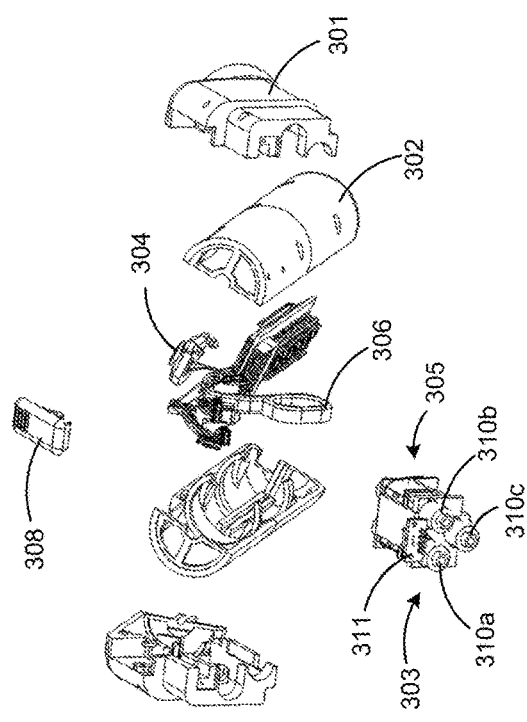
FIG. 8B
FIG. 8D
FIG. 8A
FIG. 8C

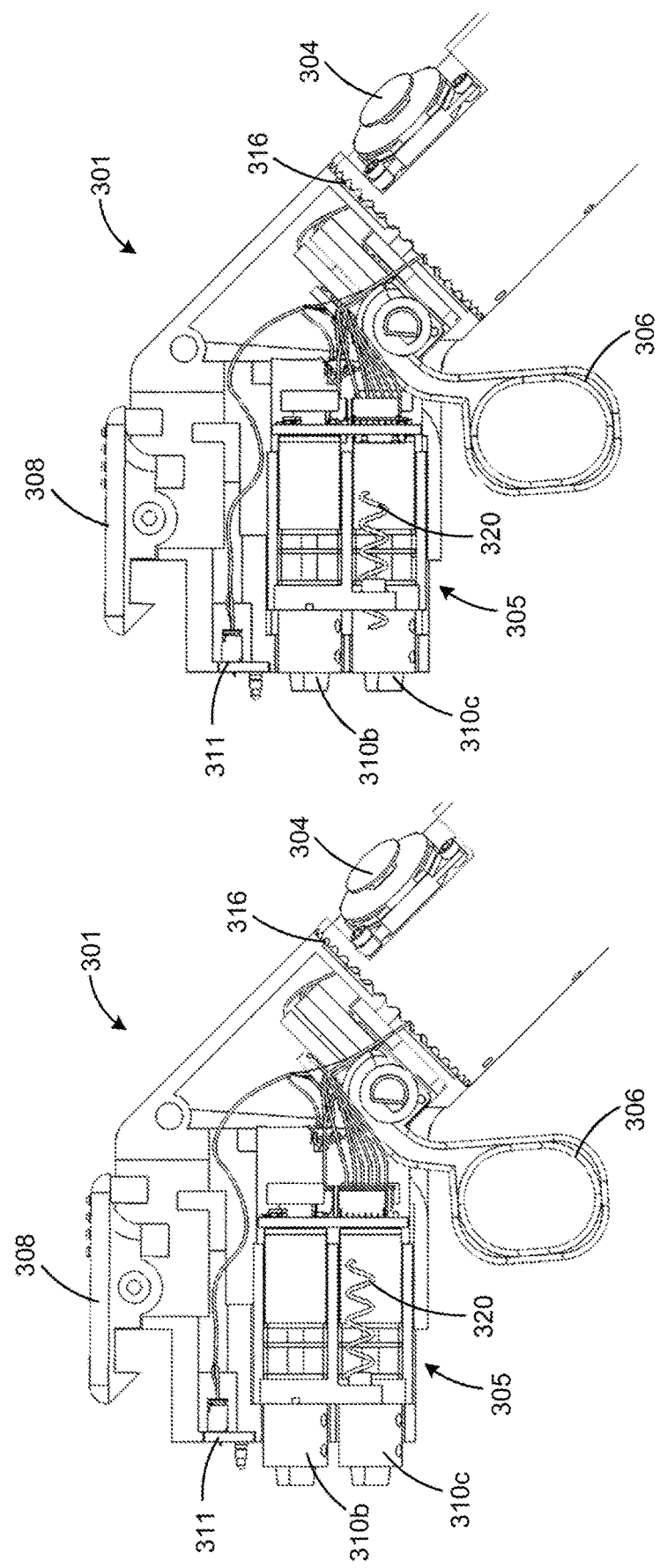

HANDHELD SURGICAL SYSTEMS WITH INTERCHANGEABLE DEXTEROUS END-EFFECTORS

CROSS-REFERENCE TO RELATED APPLICATIONS

This application is a continuation of U.S. patent application Ser. No. 18/792,533, filed Aug. 1, 2024, now U.S. Pat. No. 12,150,729, which claims priority to U.S. Provisional Patent Application No. 63/570,158, filed Mar. 26, 2024, and to European Patent Application No. 24386010.3, filed Feb. 2, 2024, the entire contents of each of which are incorporated herein by reference.

FIELD OF USE

The present technology is directed to handheld robotic systems for performing surgery, such as systems with a handheld controller with a moveable joystick, and/or interchangeable surgical instruments with dexterous end-effectors.

BACKGROUND

Since the early 1980s when it was first introduced, Minimally Invasive Surgery (MIS) has had a great deal of success. Compared to traditional surgery, it requires smaller incisions, which equates to less trauma and thus reduced pain and hospital time, making MIS the standard and established procedure in a number of operations, with laparoscopic surgery being a prime example. Albeit their numerous advantages, MIS procedures are ergonomically difficult to perform due to the use of rigid instruments, visuomotor axes misalignment, limited sensory feedback, and the need for high dexterity. Those drawbacks led to the development of robotic surgical devices that are now causing a paradigm shift in surgery.

Robotic-Assisted Minimally Invasive Surgery (RAMIS) has had a great impact since it allows for precise and accurate motions while reducing the learning curve for the surgeons. This can potentially allow more surgeons to perform MIS procedures without needing to resort to open surgery. With the introduction of robotics into the surgical scene, a number of conventional specialties, such as urology, gynecology, abdominal and cardiothoracic surgery, have integrated current robotic technologies into their procedures augmenting the capabilities of the surgeon while improving patient outcomes. Lately, an increasing amount of surgical procedures have deployed or started deploying robotic devices, with neurosurgery being at the forefront of these disciplines.

Due to its delicate subject matter and challenging operations, neurosurgery has been always in need for adapting new techniques and technologies. One such adaptation is surgical robotics, both in brain and spine applications. Although the majority of neurosurgical robots are stereotactic, technological advances in image guidance, endoscopy, and laparoscopic instruments have led into the development of robotic tools for minimally invasive neurosurgery. However, the use of robotics in 'keyhole' neurosurgical approaches is still rather limited.

A number of studies have taken place implementing concentric tube robotic tools. In Burgner, J. et al. "A bimanual teleoperated system for endonasal skull base surgery." (In: 2011 IEEE/RSJ international conference on intelligent robots and systems, pp. 2517-2523. IEEE (2011)), a prototype system for bimanual teleoperated endonasal skull base surgery is developed. However, there are still concerns about the distal-end dexterity of this manipulator and its grasping force and/or force-sensing capability.

In view of the foregoing drawbacks of previously known systems and methods, there exists a need for an end-effector for an endoscopic surgical instrument capable of applying a greater force and/or that is more robust and/or that is capable of more dexterous manipulation of tissue and/or at a smaller size than known devices.

SUMMARY

The present disclosure overcomes the drawbacks of previously-known systems and methods by providing a handheld surgical system. The handheld surgical system may include an interchangeable instrument having a proximal region and a distal region, and a handheld controller configured to be releasably coupled to the interchangeable instrument. The interchangeable instrument may comprise an elongated shaft extending between the proximal and distal regions, one or more capstan shafts disposed at the proximal region, each capstan shaft comprising a pair of capstans configured to be operatively coupled to a pair of pulleys, an end-effector disposed at the distal region, the end-effector configured to be actuated in one or more degrees of freedom, and one or more pairs of tendons. Each pair of tendons may have distal ends coupled to the end-effector and proximal ends extending through the elongated shaft towards a corresponding pair of capstans of the one or more capstan shafts via the pair of pulleys associated with the corresponding pair of capstans.

Moreover, the proximal ends may be coupled to the corresponding pair of capstans in a manner such that rotation of the corresponding capstan shaft in a first rotational direction causes a first tendon of the pair of tendons to move in a first axial direction and causes a second tendon of the pair of tendons to move in a second axial direction opposite the first axial direction to thereby actuate the end-effector in one of the one or more degrees of freedoms. Similarly, rotation of the corresponding capstan shaft in a second rotational direction opposite the first rotational direction may cause the first tendon of the pair of tendons to move in the second axial direction and may cause the second tendon of the pair of tendons to move in the first axial direction to thereby actuate the end-effector in the one of the one or more degrees of freedoms. In addition, the handheld controller may comprise an interface operatively coupled to one or more motors, the interface configured to be actuated to cause at least one of the one or more motors to cause rotation of at least one of the one or more capstan shafts to thereby actuate the end-effector in at least one of the one or more degrees of freedoms.

The one or more capstan shafts may comprise a first capstan shaft comprising a first pair of capstans operatively coupled to the end-effector via a first pair of tendons of the one or more pairs of tendon, the first capstan shaft configured to be rotated via a first motor of the one or more motors upon actuation of the interface to thereby actuate the end-effector in a pitch degree of freedom. Moreover, the one or more capstan shafts may comprise a second capstan shaft comprising a second pair of capstans operatively coupled to the end-effector via a second pair of tendons of the one or more pairs of tendons, the second capstan shaft configured to be rotated via a second motor of the one or more motors upon actuation of the interface to thereby actuate the end-effector in a yaw degree of freedom. For example, distal ends of the first pair of tendons may be coupled to opposite sides of the end-effector and configured to be actuated to cause rotation of the end-effector about a pitch axis, and distal ends of the second pair of tendons may be coupled to opposite sides of the end-effector and configured to be actuated to cause rotation of the end-effector about a yaw axis. The first and second capstan shafts may be arranged in a linear configuration. In some embodiments, the one or more capstan shafts may comprise a third capstan shaft comprising a third pair of capstans operatively coupled to the end-effector via a third pair of tendons of the one or more pairs of tendons, the third capstan shaft configured to be rotated to thereby actuate the end-effector in an open and close degree of freedom.

The handheld controller may comprise a second interface, e.g., a trigger, operatively coupled to a third motor, the second interface configured to be actuated to cause the third motor to cause rotation of the third capstan shaft to thereby actuate the end-effector in the open and close degree of freedom. Moreover, the end-effector may comprise a jaw configured to rotate about a jaw axis perpendicular to a longitudinal axis of the end-effector. Accordingly, a first distal end of a first tendon of the third pair of tendons may be coupled to a first side of the jaw and a second distal end of a second tendon of the third pair of tendons is coupled to an opposite side of the jaw, such that rotation of the third capstan shaft in the first rotational direction causes the first and second tendons of the third pair of tendons to rotate the jaw in a first direction about the jaw axis and rotation of the third capstan shaft in an opposite rotational direction causes the first and second tendons of the third pair of tendons to rotate the jaw in an opposite direction about the jaw axis. The first, second, and third capstan shafts may be arranged in a triangular configuration.

Each capstan shaft of the one or more capstan shafts may comprise an instrument coupler, and each motor of the one or more motors may comprise a controller coupler configured to be operatively coupled to a corresponding instrument coupler of the one or more capstan shafts when the handheld controller is releasably coupled to the interchangeable instrument, such that the one or more motors may be configured to cause rotation of the one or more capstan shafts via the corresponding instrument and controller couplers. Moreover, the instrument coupler may comprise a groove, and the controller coupler may comprise a boss configured to be releasably engaged with the groove to transmit rotary motion from one or more motors to the one or more capstan shafts. The boss may comprise a tapered portion configured to facilitate self-alignment of the controller coupler with the instrument coupler. Additionally, the one or more motors may be disposed within a compliant motor pack configured to move within the handheld controller responsive to a force to facilitate self-alignment of the controller coupler with the instrument coupler.

In some embodiments, each capstan shaft of the one or more capstan shafts may be configured to rotate about a respective capstan axis parallel to a longitudinal axis of the elongated shaft. In addition, each pair of pulleys associated with the one or more capstan shafts may be configured to rotate about a respective pulley axis perpendicular to the longitudinal axis of the elongated shaft. The respective pulley axis may be angled to align each pair of pulleys in a direction towards the pair of capstans of the associated one or more capstan shafts. Moreover, each pair of pulleys associated with the one or more capstan shafts may be aligned with the longitudinal axis of the elongated shaft to thereby route the one or more pairs of tendons from the one or more capstan shafts through the elongated shaft. For example, a first pair of pulleys associated with a first capstan shaft of the one or more capstan shafts may be configured to rotate about a first pulley axis, and a second pair of pulleys associated with a second capstan shaft of the one or more capstan shafts may be configured to rotate about a second pulley axis offset from the first pulley axis.

The elongated shaft may comprise one or more channels extending therethrough, each channel sized and shaped to receive a tendon of the one or more pairs of tendons. In some embodiments, a distal end of the elongated shaft may comprise a ball joint base, and a proximal end of the end-effector may comprise a ball configured to pivotally engage the ball joint base to form a ball joint configured to permit movement of the end-effector in two degrees of freedom about the ball joint. The handheld surgical system further may include a latch configured to be actuated to transition between an unlocked state and a locked state to thereby lock the handheld controller to the interchangeable instrument. The elongated shaft may comprise an angled shaft. In addition, the interchangeable instrument may comprise one or more sensors configured to measure an angular position of each capstan shaft of the one or more capstan shafts, the angular position of each capstan shaft indicative of an amount of actuation of the end-effector in each of the one or more degrees of freedoms. The interface may comprise a joystick.

Moreover, the handheld controller may comprise a connection portion configured to be removably coupled to the interchangeable instrument, and a handle portion rotatably coupled to the connection portion. The handle portion may be sized and shaped to be held in a user's palm and may comprise the interface. Accordingly, the handle portion may be configured to be selectively rotated relative to the connection portion at predefined increments to ergonomically align the interface with the user's thumb. For example, the handle portion may be rotatably coupled to the connection portion via a joint, e.g., a hirth joint, and the handle portion may be coupled to the connection portion via a compression spring configured to bias the handle portion towards the connection portion to thereby maintain a position of the handle position relative to the connection portion. The compression spring may comprise a spring cap configured to provide a stable compression position of the compression spring within the handle portion The handheld controller further may comprise a second interface configured to be actuated to cause the end-effector to return to a linear configuration. The end-effector may comprise a long grasper, a short grasper, a ring-curette, a long ring-curette, a spoon curette, a suction tip, an endoscope, a needle holder, a scissor, or a dissector, etc. The handheld surgical system further may include a console configured to be operatively coupled to the handheld controller. For example, the console may be configured to provide power to the handheld controller. Moreover, the console may be configured to adjust one or more parameters of the handheld controller responsive to user input received at the console.

In accordance with another aspect of the present disclosure, a handheld controller for releasably coupling to an interchangeable instrument having an end-effector is provided. The handheld controller may include a connection portion configured to be releasably coupled to the interchangeable instrument having the end-effector for performing surgery, a handle portion rotatably coupled to the connection portion via a joint, e.g., a hirth joint, the handle portion sized and shaped to be held in a user's palm, an interface, e.g., a joystick, disposed on the handle portion, the interface configured to be actuated to move the end-effector in one or more degrees of freedom when the interchangeable instrument is releasably coupled to the handheld controller, and a compression spring configured to bias the handle portion towards the connection portion to thereby maintain a position of the handle position relative to the connection portion. Accordingly, the handle portion may be configured to be selectively rotated relative to the connection portion at predefined increments to ergonomically align the interface with the user's thumb.

For example, a proximal end of the connection portion may comprise a first hirth gear, and a distal end of the handle portion may comprise a second hirth gear configured to releasably engage the first hirth gear at the predefined increments to thereby form the hirth joint. The compression spring may comprise a spring cap configured to provide a stable compression position of the compression spring within the handle portion and to prevent over-pulling of the handle portion relative to the connection portion. In addition, the connection portion may comprise a latch configured to releasably engage a groove of the interchangeable instrument when the handheld controller is releasably coupled to the interchangeable handle to thereby lock the handheld controller to the interchangeable instrument.

The connection portion further may comprise an electrical connector configured to be operatively coupled to a corresponding electrical connector of the interchangeable instrument when the interchangeable instrument is releasably coupled to the handheld controller to thereby transmit electrical signals and power between the handheld controller and interchangeable instrument. The handheld controller further may comprise a controller operatively coupled to the electrical connector of the handheld controller, The controller may be configured to receive instrument specific configuration data associated with the interchangeable instrument via the electrical connector of the handheld controller when the interchangeable instrument is releasably coupled to the handheld controller. For example, the instrument specific configuration data may comprise information indicative of instrument type, instrument specifications, and/or instrument capabilities.

The handheld controller further may comprise one or more motors disposed within the connection portion, the one or more motors configured to be individually actuated to cause movement of the end-effector in the one or more degrees of freedom when the interchangeable instrument is releasably coupled to the handheld controller. For example, the one or more motors may comprise a first motor operatively coupled the interface, and a second motor operatively coupled the interface. The first motor may be configured to be actuated via the interface to cause movement of the end-effector in a first degree of freedom of the one or more degrees of freedom, e.g., a pitch degree of freedom, when the interchangeable instrument is releasably coupled to the handheld controller, and the second motor may be configured to be actuated via the interface to cause movement of the end-effector in a second degree of freedom of the one or more degrees of freedom, e.g., a yaw degree of freedom, when the interchangeable instrument is releasably coupled to the handheld controller.

In some embodiments, the handheld controller further may comprise a second interface, e.g., a trigger, configured to be actuated to move the end-effector in a third degree of freedom of the one or more degrees of freedom, e.g., an open and close degree of freedom, when the interchangeable instrument is releasably coupled to the handheld controller. Accordingly, the one or more motors may comprise a third motor operatively coupled the second interface, the third motor configured to be actuated via the interface to cause movement of the end-effector in the third degree of freedom. The second interface may be disposed on the connection portion. Moreover, the first, second, and third motors may comprise first, second, and third controller couplers, respectively, the first, second, and third controller couplers configured to be operatively coupled to corresponding instrument couplers of the interchangeable instrument when the interchangeable instrument is releasably coupled to the handheld controller to thereby transmit rotary motion from the first, second, and third motors to the corresponding instrument couplers to cause movement of the end-effector in the first, second, and third degrees of freedom. The first and second controller couplers may be arranged in a linear configuration. Additionally, the third controller coupler may be arranged in a triangular configuration relative to the first and second controller couplers.

In accordance with yet another aspect of the present disclosure, a handheld controller for releasably coupling to an interchangeable instrument having an end-effector coupled to one or more capstan shafts via a tendon routing system is provided. The handheld controller may comprise one or more controller couplers operatively coupled to one or more motors, each of the one or more controller couplers comprising a boss configured to be releasably engaged with a groove of a corresponding instrument coupler of the one or more capstan shafts when the interchangeable instrument is releasably coupled to the handheld controller to transmit rotary motion from the one or more motors to the one or more capstan shafts. Moreover, the boss may comprise a tapered portion configured to facilitate self-alignment of the one or more controller coupler with the corresponding instrument couplers. For example, a cross-sectional area of the tapered portion of the boss may decrease in a distal direction from the handheld controller towards the instrument couplers when the interchangeable instrument is releasably coupled to the handheld controller.

The boss may comprise a first geometry corresponding to a second geometry of the groove of the corresponding instrument coupler, such that, when the boss is releasably engaged with the groove, relative rotation between the one or more controller couplers and the corresponding instrument couplers is prohibited. In addition, the first and second geometries may comprise a profile having multiple lines of symmetry intersecting an axis of rotation of the one or more controller couplers. For example, the profile may comprise a hexagonal shape. Moreover, at least one of the one or more controller couplers or the corresponding instrument couplers may be configured to rotate relative to one another upon engagement of the tapered portion of the boss with the groove as the interchangeable instrument is releasably coupled to the handheld controller to thereby facilitate self-alignment of the one or more controller couplers with the corresponding instrument couplers.

In some embodiments, the one or more controller couplers may be configured to be slidably movable translationally between a retracted position and an extended position. For example, the handheld controller may comprise one or more compression springs configured to bias the one or more controller couplers towards the extended position to facilitate self-alignment of the one or more controller couplers with the corresponding instrument couplers. In addition, the handheld controller may comprise one or more interfaces operatively coupled to the one or more motors, the one or more interfaces configured to be actuated to cause the one or more motors to rotate the one or more controller couplers to thereby transmit rotary motion from the one or more motors to the one or more capstans shafts via the corresponding instrument couplers when the interchangeable instrument is releasably coupled to the handheld controller. Accordingly, when the one or more controller couplers are in the retracted position, actuation of the one or more interfaces may cause rotation of the one or more controller couplers relative to the corresponding instrument couplers to thereby facilitate engagement between the boss of the one or more controller couplers and the groove of the corresponding instrument couplers.

In accordance with another aspect of the present disclosure, a handheld controller for releasably coupling to an interchangeable instrument having an end-effector coupled to one or more capstan shafts via a tendon routing system is provided. The handheld controller may comprise a connection portion configured to be releasably coupled to the interchangeable instrument, one or more motors slidably disposed within the connection portion between a retracted position and an extended position, the one or more motors configured to actuate the one or more capstan shafts when the interchangeable instrument is releasably coupled to the handheld controller, and one or more compression springs coupled to the one or more motors, the one or more compression springs configured to bias the one or more motors towards the extended position to facilitate coupling of the handheld controller to the interchangeable instrument. The handheld controller further may comprise one or more controller couplers operatively coupled to the one or more motors, each of the one or more controller couplers comprising a boss configured to be releasably engaged with a groove of a corresponding instrument coupler of the one or more capstan shafts when the interchangeable instrument is releasably coupled to the handheld controller to transmit rotary motion from the one or more motors to the one or more capstan shafts. Moreover, the boss may comprise a tapered portion configured to facilitate self-alignment of the one or more controller coupler with the corresponding instrument couplers.

BRIEF DESCRIPTION OF THE DRAWINGS

FIGS. 8A to 8D illustrate an exemplary handheld controller of the handheld surgical system constructed in accordance with the principles of the present disclosure.

FIGS. 9A and 9B illustrate the internal components of an exemplary connection portion of the handheld controller constructed in accordance with the principles of the present disclosure.

DETAILED DESCRIPTION

Figure 1A:
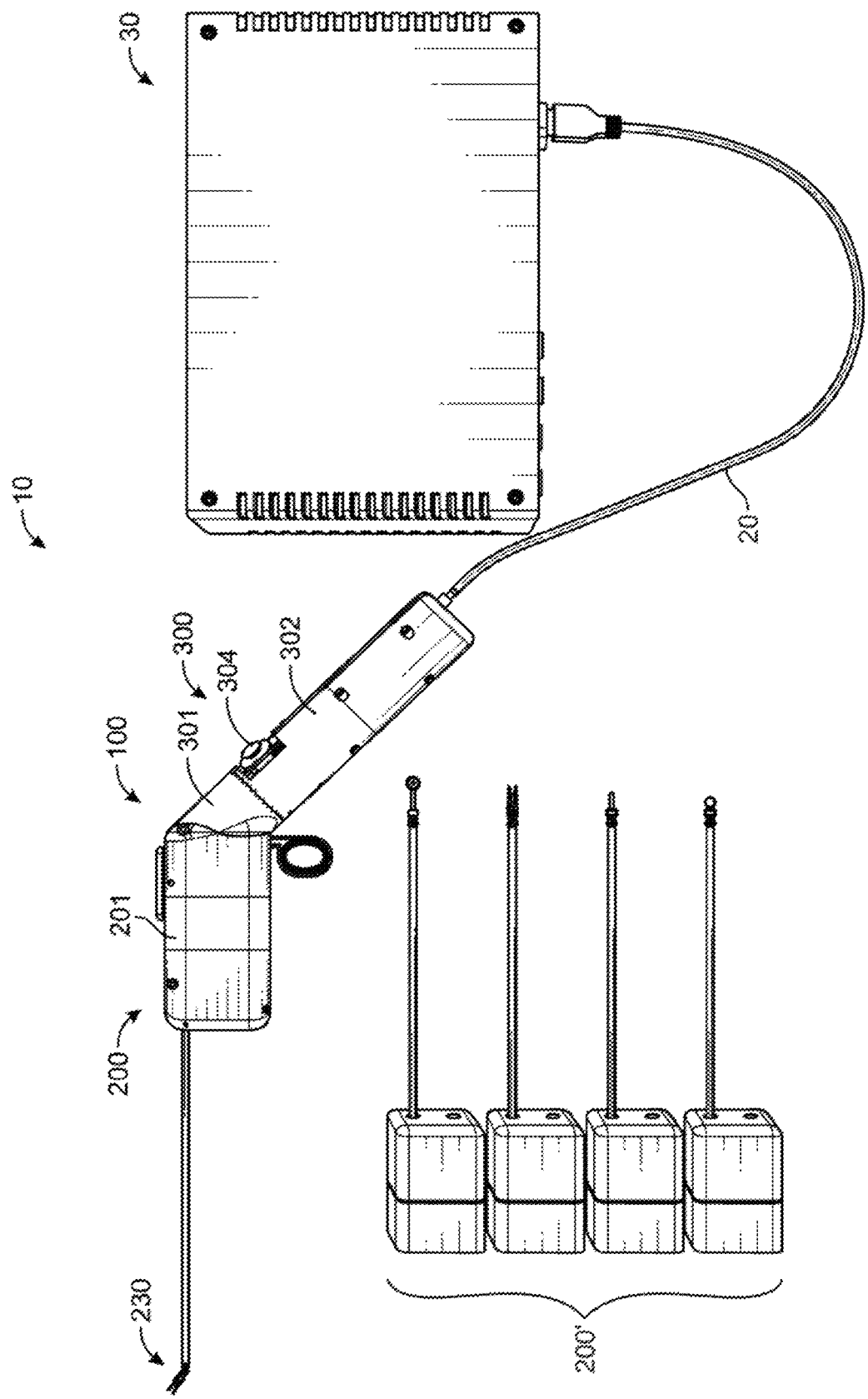
FIG. 1A illustrates an exemplary handheld surgical system with an interchangeable, dexterous end-effector in accordance with the principles of the present disclosure.

Disclosed herein are handheld surgical systems having an adjustable, ergonomic handheld controller and a series of interchangeable surgical instruments with dexterous, flexible tips (e.g., end-effectors such as graspers, scissors, curettes, dissectors, etc.) for performing a surgical procedure, e.g., removing brain tumor tissue from confined spaces, and methods of use thereof. For example, the interchangeable instruments may have flexible tips with a maximum diameter of, e.g., 3 mm, that may rotate in the pitch and yaw axes, and allow the user precise soft tissue resection and manipulation. The interchangeable instruments may be easily detached and reattached to the handheld controller as needed, are provided sterile, and may be disposed of after a single use. Alternatively, the interchangeable instruments may be sterilizeable and reusable. The handheld controller may be reusable and may be used in surgical procedures with a custom drape configured to incorporate sterile adapters for the motors and control interfaces of the handheld surgical system. The handheld surgical system is lightweight, and preferably weighs no more than 300 grams.

Each interchangeable instrument may include a flexible distal end ball-and-socket joint that may move in the pitch and yaw axes, a rigid straight shaft, and an instrument housing which encloses the capstan and routing system, as described below. The interchangeable instruments may have an overall weight of, e.g., about 100 g, and may be split into 2 degrees of freedom (DOF) and 3 DOF instruments. The 2

DOF instruments may rotate about two axes, e.g., pitch and yaw; whereas, the 3 DOF instruments may rotate about two axes, e.g., pitch and yaw, and further may be actuated to open or close. Both types of instruments may use the ball joint which may have through holes for the antagonistic actuation wires. With rotation about both axes and the surgeon's hand complementing with the roll-axis movement, a full wrist-like articulation may be achieved. These precisely controlled instruments may accurately remove pieces of soft tissue via grasping, cutting, or massaging motions.

The flexible instrument tips are driven by a routing system located inside the instrument housing. The routing system may be directly actuated by two or three motors, depending on the instrument function, housed inside the handheld controller. For example, if the interchangeable instrument is a curette or a dissector, which does not require an additional grasping or cutting motion, only two motors may be used. For graspers and scissors, a third motor may control the grasping and cutting movements. Additionally, the electronics that drive the motors and implement the device control also may be housed inside the handheld controller.

At the console end, a power supply with a single-board computer may be used to provide power and any communication needed for the tethered handheld controller. On the handheld controller, a joystick, buttons, and a trigger may be used for user input. The joystick is a main interface with the user and controls the pitch and yaw actuation of the flexible joint. For example, the joystick rests on a rotating handle body that may be selectively moved in position by the user. Depending on the user's hand size, or whether they are right- or left-handed, the user may rotate the movable handle into the position they find most comfortable. This may happen pre-operatively and does not affect the movement of the instrument tip. The position of the joystick may only cater to the user's comfort and intuitiveness. Additionally, the mechanism for the joystick that is on a moveable handle body uses a compression spring in conjunction with mating hirth gear teeth. Accordingly, the rotating handle may be pulled back, rotated, and finally released with the hirth gears on the rotating handle and controller side meshing to provide rotational rigidity.

Moreover, the trigger may be actuated to control grasping, a button may be actuated to return the instrument tip to its neutral position, and an actuator, e.g., a digital switch, may be actuated to initiate the coupling/decoupling process of the instrument. The coupling process may use a spring-loaded latch that fixes the interchangeable instrument on the handheld controller. The handheld surgical systems described herein are configured to work in conjunction with commercially available standard neuroendoscopes (e.g., made available by Karl Storz, Tuttlingen, Germany) that may provide direct visualization of the operative workspace, and standard suction tips (e.g., made available by B. Braun, Melsungen, Germany) that may remove any tumor tissue pieces that the handheld surgical system has resected.

To provide a detailed description of the mechanisms and principles of operation, the system may be separated into four systems as seen in Table 1: the flexible instruments, handheld controller, routing system, and console.

TABLE 1

| Component | Description |
| --- | --- |
| Interchangeable instrument | A series of interchangeable instruments with flexible miniature tips. Their purpose is to manipulate and resect soft tissue, and they can precisely rotate left/right and up/down (e.g., curettes or dissectors), whereas some can also open and close (e.g., graspers and scissors). The instrument is connected to the handheld controller.<br>The instrument includes a tendon routing system. The routing system is the path of the wires or tendons through the handheld unit. This is the main mechanism for pushing and pulling. |
| Handheld controller | A handheld unit with a joystick controller, a trigger, and two buttons, that control the instrument. The user moves the joystick to control the instrument tip, whereas the trigger provides opening/closing motions. The handheld controller is connected to the console. |
| Console | The console provides power to the handheld controller so that the latter can move the instrument tip via the joystick/trigger/button interfaces. The console also provides quick configuration inputs, such as variable instrument tip speeds. It is connected to the building's power supply. |

Figure 1B:
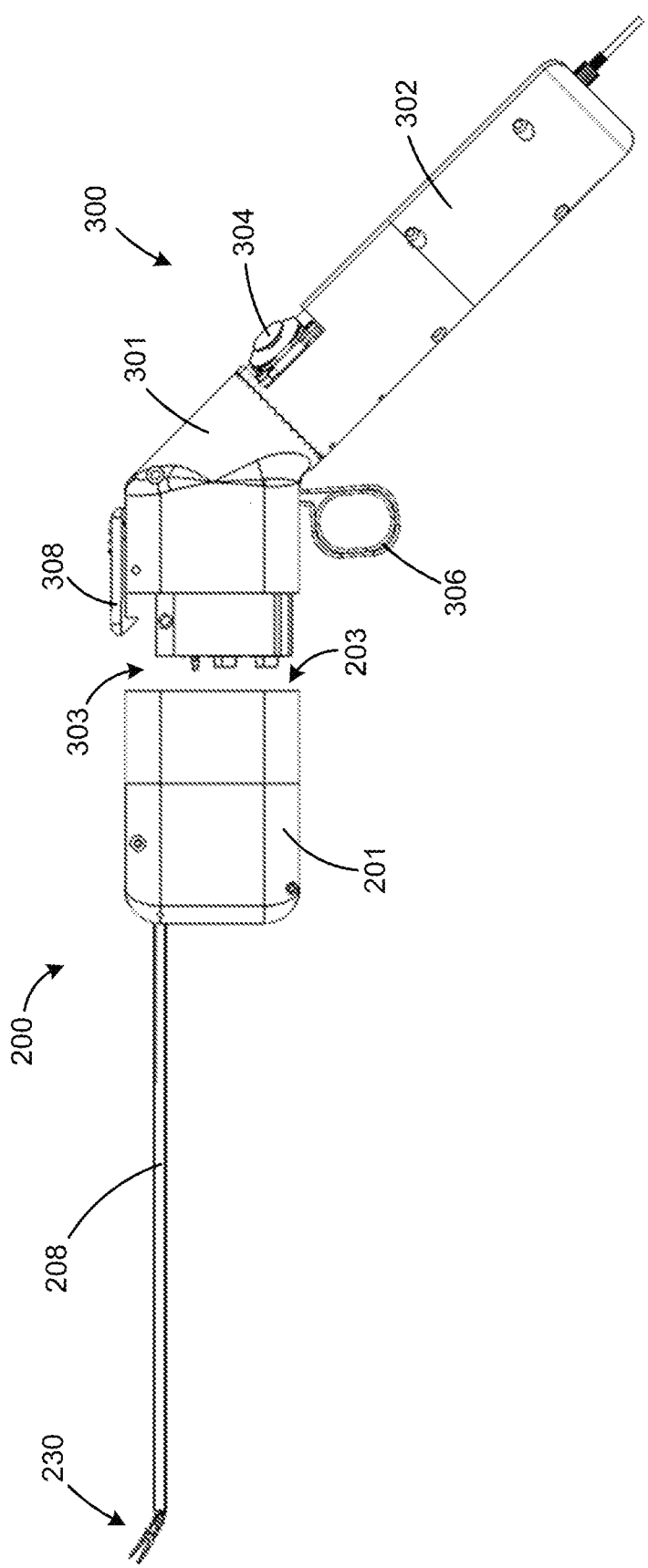
FIG. 1B illustrates the handheld controller and interchangeable instrument of FIG. 1A in a disengaged state.

Referring now to FIGS. 1A and 1B, an exemplary handheld surgical system is provided. As shown in FIG. 1A, system 10 may include handheld surgical system 100 having handheld controller 300 with moveable joystick 304, and a series of interchangeable surgical instruments 200, 200' configured to be removably coupled to handheld controller 300 via a coupling interface, each interchangeable instrument having elongated shaft 208 and a dexterous end-effector actuatable via a tendon routing system, as described in further detail below. As will be understood by a person having ordinary skill in the art, while FIG. 1B illustrates elongated shaft 208 having a linear configuration along its entire length, in some embodiments, elongated shaft 208 may be an angled shaft. System 10 further may include console 30 operatively coupled to handheld surgical system 100 via cable 20 for providing power and tuning to system 100, e.g., for sending command signals to the microcontroller of handheld controller 300 for controlling the dexterous end-effectors of interchangeable instruments 200, 200' when removably coupled to handheld controller 300.

FIG. 1B illustrates handheld surgical system 100 in a disengaged state where coupling interface 203 of interchangeable instrument 200 is decoupled from coupling interface 303 of handheld controller 300. Accordingly, interchangeable instrument 200 may be exchanged/replaced with another interchangeable surgical instrument for removably coupling with handheld controller 300, depending on the tool requirements of the surgical procedure to be performed via handheld surgical system 100. For example, each interchangeable surgical instrument may have an end-effector configured to be actuated in two degrees of freedom, e.g., pitch and/or yaw, or three degrees of freedom, e.g., pitch, yaw, and/or open/close. Accordingly, handheld controller 300 may comprise a series of interfaces, e.g., joystick 304 and trigger 306, configured to receive user input and cause the interchangeable surgical instrument coupled to handheld control 300 to actuate its end-effector in a corresponding degree of freedom. For example, joystick 304 may be actuated, e.g., moved up/down and/or left/right, to control actuation of end-effector 230 in the pitch and yaw degrees of freedom, respectively, while trigger 306 may be actuated to control the actuation of end-effector 230 in the open/close degree of freedom, e.g., grasping/cutting.

As shown in FIG. 1B, handheld controller 300 may include connection portion 301 having coupling interface 303 configured to removably couple to coupler interface 203 of interchangeable instrument 200, and handle portion 302 having joystick 304 disposed thereon. Handle portion 302 may have a large surface area allowing the user to grasp it firmly with their dominant hand, allowing for easy maneuverability and dexterity. Moreover, handle portion 302 may be configured to be selectively rotated relative to connection portion 301 of handheld controller 300 to thereby adjust the position of joystick 304 on handheld controller 300, e.g., relative to connection portion 301, to ergonomically accommodate the preferences of different users. For example, joystick 304 preferably may be actuatable via the user's thumb, e.g., the thumb of the user's right or left hand, such that the position of joystick 304 may be adjusted based on user comfort and thumb extension.

Figure 2A:
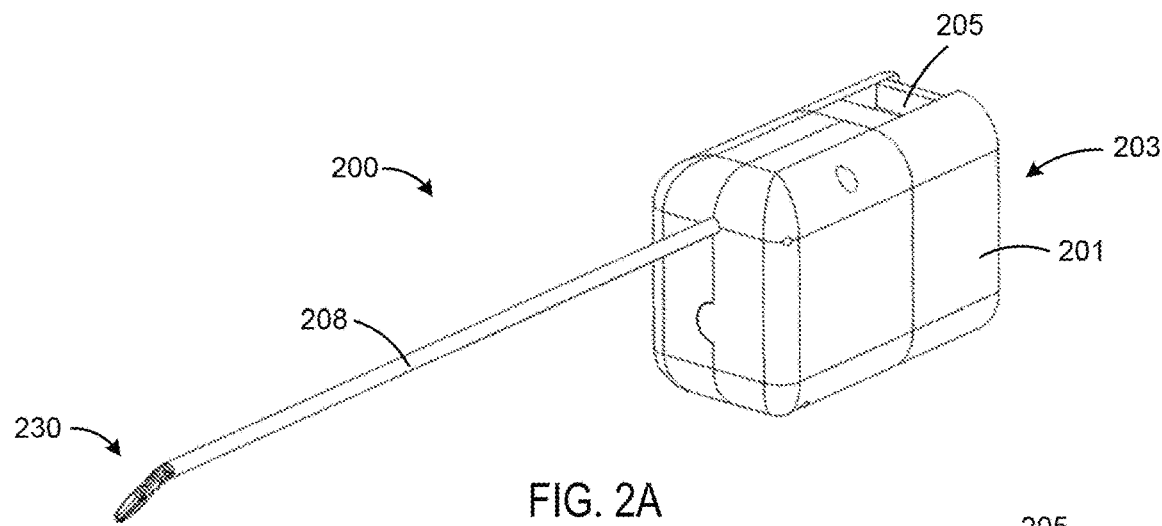
FIG. 2A illustrates an exemplary interchangeable instrument of the handheld surgical system constructed in accordance with the principles of the present disclosure.
Figure 2B:
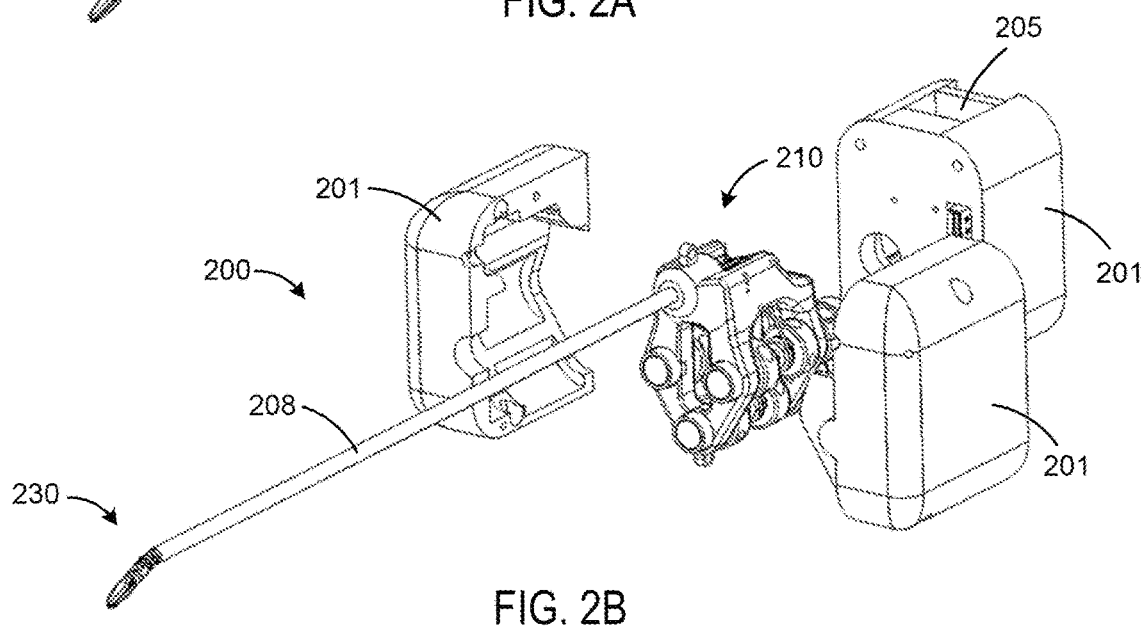
FIGS. 2B and 2C are an exploded view of the interchangeable instrument of FIG. 2A.
Figure 2C:
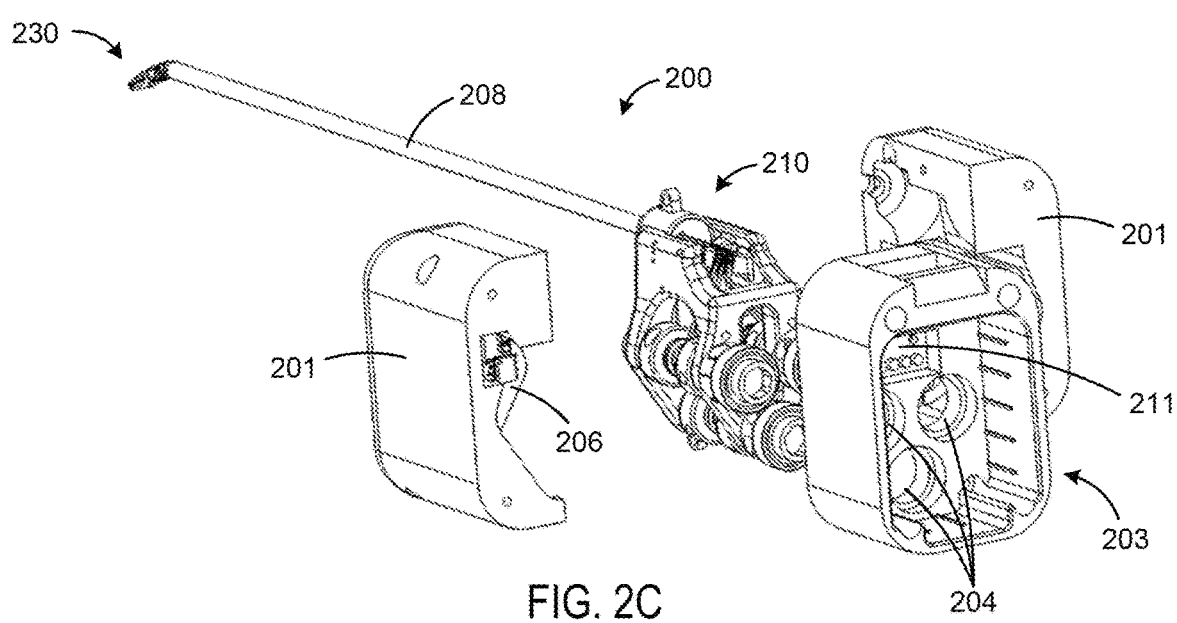

Referring now to FIGS. 2A to 2C, an exemplary interchangeable surgical instrument is provided. As shown in FIG. 2A, interchangeable surgical instrument 200 may include housing 201, elongated shaft 208 extending distally from housing 201, and end-effector 230 disposed at the distal end of elongated shaft 208. Elongated shaft 208 may have one or more lumens/channels extending therethrough, each sized and shaped to slidably receive corresponding tendons of the tendon routing system of interchangeable instrument 200 extending from housing 201 to end-effector 230. In addition, housing 201 may include groove 205, e.g., a receptacle, configured to releasably engage with latch 308 of connection portion 301 of handheld controller 300 to thereby lock interchangeable instrument 200 to handheld controller 300, as described in further detail below. As shown in FIGS. 2B and 2C, housing 201 may be sized and shaped to house tendon routing system 210 therein. Housing 201 further may house the electronic components of interchangeable instrument 200, e.g., circuit board 206 configured to measure and store the position/orientation of the capstan shafts of tendon routing system 210, as described in further detail below.

As shown in FIG. 2C, housing 201 may include coupling interface 203 for removably coupled tendon routing system 210 to coupler interface 303 of handheld controller 300. For example, coupling interface 203 may include a plurality of openings 204, each sized and shaped to receive a corresponding instrument coupler of tendon routing system 210 therethrough for removable coupling with a corresponding controller coupler of handheld controller 300. As will be understood by a person having ordinary skill in the art, while FIG. 2C shows three openings 204, coupling interface 203 may have a number of openings corresponding with the number of degrees of freedom the end-effector of the interchangeable instrument may be actuating in. For example, as described in further detail below, tendon routing system 210 of interchangeable instrument 200 may have a plurality of capstan shafts, each capstan shaft comprising a pair of capstans configured to control actuation of end-effector 203 in a single degree of freedom, and each capstan shaft having an instrument coupler. Accordingly, an interchangeable instrument having an end-effector actuatable in two degrees of freedom may have only two capstan shafts, e.g., two pairs of capstans, and accordingly, two instrument couplers, and thus, coupling interface 203 may have only two openings 204. Moreover, as shown in FIG. 2C, coupling interface 203 further may include electrical connector 211 configured to be electrically connected to a corresponding electrical connector of handheld controller 300, to thereby transmit electrical signals and power between handheld controller 300 and interchangeable instrument 200.

Referring now to FIGS. 3A to 3D, an exemplary capstan arrangement of tendon routing system 210 is provided. As described above, end-effector 230 of interchangeable instrument 200 may be actuated, e.g., rotated in the yaw and pitch degrees of freedom and/or the open/close degree of freedom, via tendons (e.g., wires) extending from end-effector 230, through elongated shaft 208, to tendon routing system 210 disposed within housing 201 of interchangeable instrument 200. For example, each actuatable degree of freedom of end-effector 230 may be controlled via a designated pair of antagonistic tendons, e.g., tendons 216a, 216b, 216c (collectively referred to herein as tendons 216). Each tendon may be, e.g., a braided wire, and may have a diameter of, e.g., 0.3 mm. Moreover, each pair of tendons 216a, 216b, 216c travel from the distal end of interchangeable instrument 200, all the way to the proximal end of interchangeable instrument 200, where they are routed via tendon routing system 210 within housing 201 to terminate on a series of capstans. For example, each pair of antagonistic tendons 216a, 216b, 216c, may be operatively coupled to a designated pair of capstans disposed on a capstan shaft, e.g., a first tendon of a pair of antagonistic tendons may be coupled to a first capstan of a pair of capstans of a first capstan shaft, and a second tendon of the pair of antagonistic tendons may be coupled to a second capstan of the pair of capstans of the first capstan shaft in an antagonistic manner such that rotation of the capstan shaft in a first direction causes the first capstan to move, e.g., pull, the first tendon in a first direction to wrap around the first capstan while simultaneously causing the second capstan to move, e.g., release, the second tendon in a second direction opposite the first direction to unwrap from the second capstan. For brevity, each capstan shaft and the corresponding pair of capstans associated therewith may be collectively referred to herein as a capstan, e.g., capstans 214a, 214b, 214c (collectively referred to herein as capstans 214). Each capstan 214a, 214b, 214c may have a coupler interface, e.g., coupler interface 218a, 218b, 218c, respectively, (collectively referred to herein as coupler interface 218), and configured to rotate about a corresponding axis of rotation, e.g., the corresponding longitudinal axis of the capstan shaft.

As shown in FIGS. 3A to 3D, the longitudinal axis of each capstan 214a, 214b, 214c may extend parallel to the longitudinal axis of elongated shaft 208. Accordingly, as described in further detail below with regard to FIGS. 4A and 4B, the pulley arrangement of tendon routing system 210 may redirect tendons 216a, 216b, 216c from each of capstans 214a, 214b, 214c, respectively, towards and through the respective channel of elongated shaft 208. Referring again to FIGS. 3A to 3D, capstans 214 may be arranged in a triangular configuration. For example, capstans 214a, 214b (e.g., for controlling the pitch and yaw degrees of freedom of end-effector 230) preferably may be arranged in a linear configuration with respect to each other, and capstan 214c (e.g., for controlling the open/close degrees of freedom of end-effector 230) may be arranged at a position offset from capstans 214a, 214b, e.g., below capstans 214a, 214b, thereby forming a triangular configuration. As will be understood by a person having ordinary skill in the art, the order of capstans within the triangular configuration may be modified, e.g., the capstan for controlling the open/close degrees of freedom may be arranged in a linear configuration with the capstan for controlling the pitch or yaw degree of freedom, while the remaining capstan is arranged in the offset position. Moreover, interchangeable instruments actuatable in only two degrees of freedom may only include two capstans, and thus may be arranged in a linear configuration within housing 201. In some embodiments, capstans 214a, 214b, 214c may be arranged in a linear configuration.

The antagonistic motion of each pair of tendons may be defined as the pulling of one tendon of the pair of tendons in a first direction, e.g., via rotation of the corresponding capstan shaft, while simultaneously pushing/releasing the other tendon of the pair of tendons in a second direction opposite the first direction, or vice versa by rotating the corresponding capstan shaft in the opposite direction, each capstan shaft having a pair of capstans. For example, the proximal ends of each pair of tendons may be coupled to and wrapped around a designated capstan of the pair of capstans in opposite directions, to thereby provide the antagonistic action of the pair of tendons upon rotation of the designated pair of capstans. For example, a first tendon of the pair of tendons may be coupled to and wrapped around a first capstan of the pair of capstans in a counter-clockwise direction, and a second tendon of the pair of tendons may be coupled to and wrapped around a second capstan of the same pair of capstans in a clockwise direction, such that, upon rotation of the capstan shaft in the counter-clockwise direction, the first tendon of the pair of tendons will be moved/pulled in a first direction towards the first capstan of the pair of capstans and further wrapped around the first capstan, while the second tendon of the pair of tendons will be moved/released in a second direction away from the second capstan of the pair of capstans while unwrapping from the second capstan.

Similarly, upon rotation of the capstan shaft in the clockwise direction, the second tendon of the pair of tendons will be moved/pulled in the first direction towards the second capstan of the pair of capstans and further wrapped around the second capstan, while the first tendon of the pair of tendons will be moved/released in the second direction away from the first capstan of the pair of capstans while unwrapping from the first capstan. Accordingly, rotation of a capstan shaft in a given direction will cause the pair of tendons to antagonistically move in equal and opposite directions from each other. Alternatively, rather than a pair of tendons coupled to a single capstan shaft for actuating the end-effector in a corresponding degree of freedom, a single tendon may be wrapped around the capstan shaft, such that the free ends of the single tendon are routed to and coupled to the end-effector. In another alternative embodiment, rather than a pair of tendons coupled to a single capstan shaft for actuating the end-effector in a corresponding degree of freedom, a single tendon may be wrapped around the end-effector link such that a first end of the single tendon may be coupled to a first capstan of a pair of capstans of a single capstan shaft, and a second end of the single tendon may be coupled to a second capstan of the pair of capstans of the single capstan shaft.

Figures 3A, 3B:
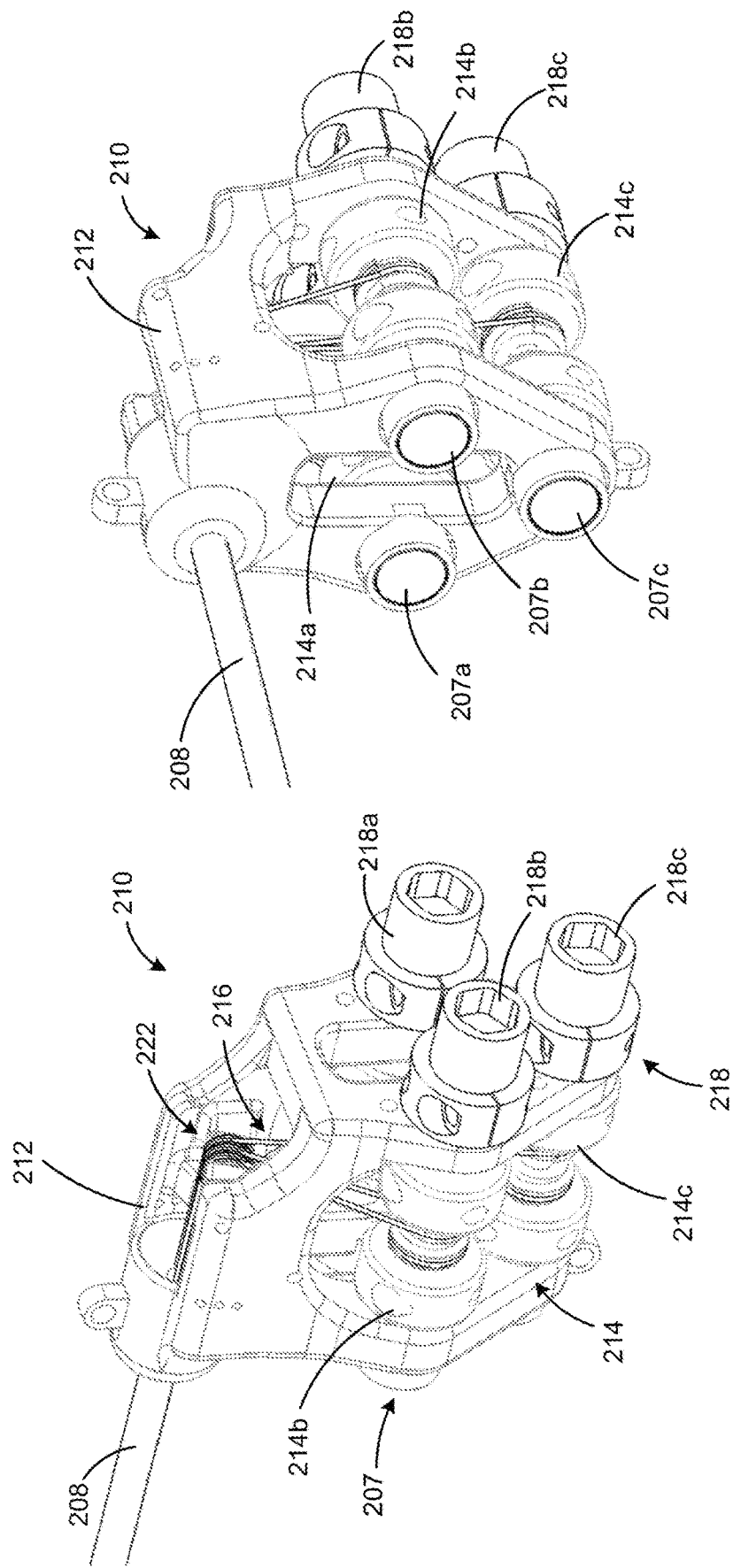
FIGS. 3A to 3D illustrate an exemplary capstan arrangement of the tendon routing system of the interchangeable instrument constructed in accordance with the principles of the present disclosure.
Figure 3D:
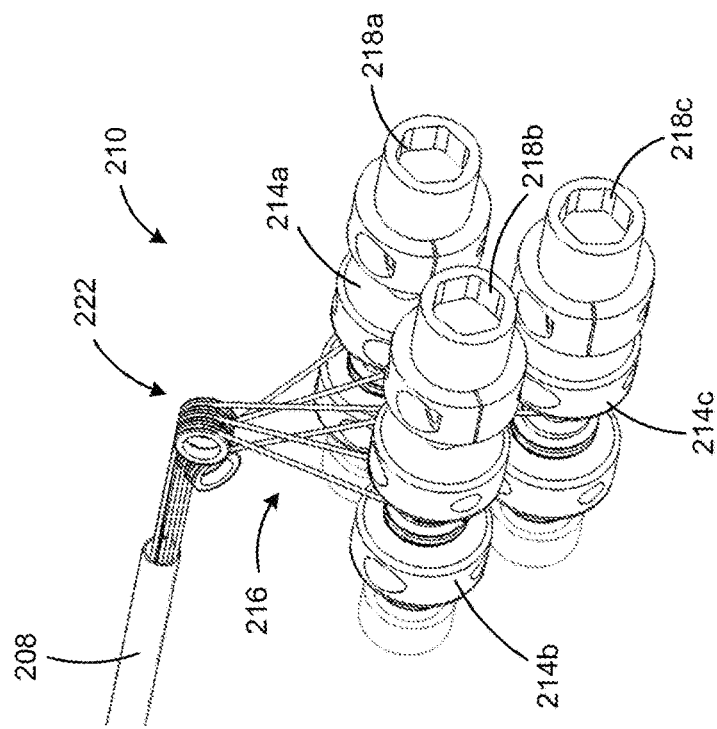

As shown in FIG. 3B, each capstan 214a, 214b, 214c may be associated with a designated capstan position resolver, e.g., capstan position resolvers 207a, 207b, 207c, respectively, (collectively referred to herein as capstan position resolver 207), each capstan position resolver configured to validate rotation, e.g., by measuring the angular rotation/position/orientation of the associated capstan shaft, and accordingly, the degree of actuation of end-effector 230 in the corresponding degree of freedom. For example, capstan position resolver 207 may be an electrical sensor configured to measure the absolute angle of capstan shaft determined against an internal reference. In some embodiments, a magnet, e.g., a circular magnet, may be fixed on each capstan shaft and may sit opposite to a corresponding magnetic encoder on circuit board 206, e.g., a magnetic encoder board, in order to measure the position of the rotating capstan shaft, which may then be translated to instrument tip angles. For example, the magnetic encoders may be configured to measure an angular position of each capstan shaft based on a magnetic field of the magnets, the angular position of each capstan shaft indicative of an amount of actuation of end-effector 230 in each of the degrees of freedoms.

Figure 3C:
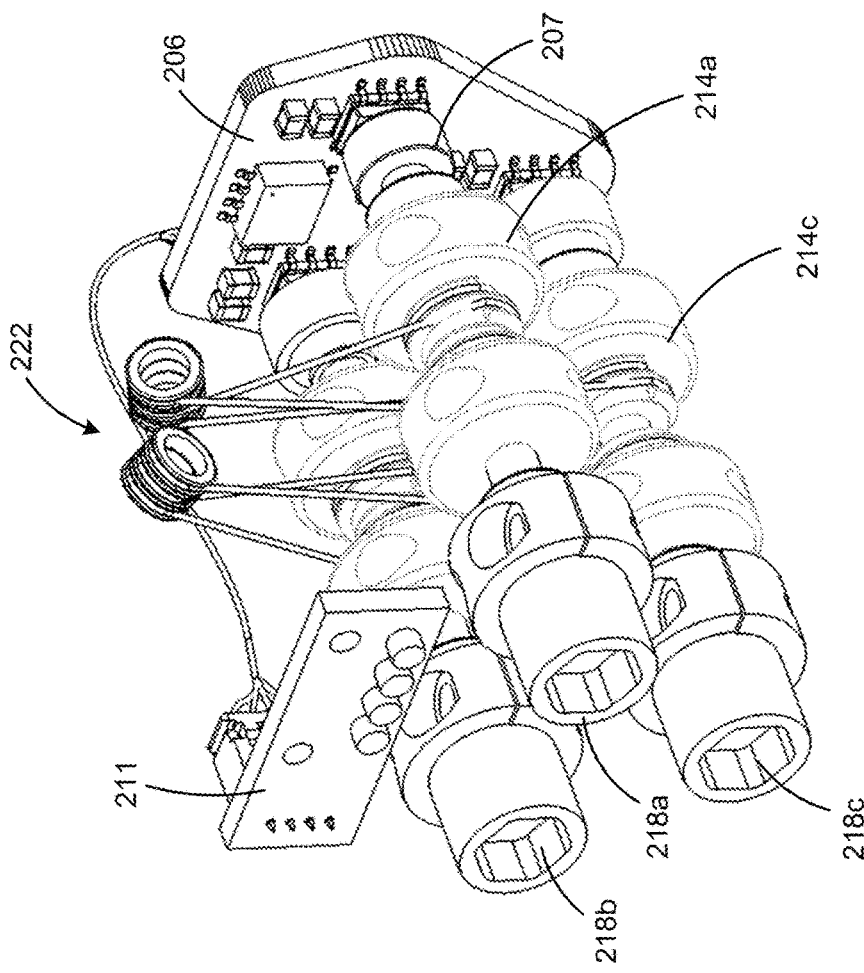

As shown in FIG. 3C, housing 201 further may house circuit board 206 having capstan position resolvers 207a, 207b, 207c arranged thereon in a manner corresponding to the arrangement of capstan position resolvers 207a, 207b, 207c, and a memory chip, e.g., for storing instrument specific configuration data loaded by handheld controller 300 when interchangeable instrument 200 is coupled with handheld controller 300. Circuit board 206 may be electrically coupled to electrical connector 211, e.g., via a cabled connection, disposed at coupling interface 203, as described above, for exposing an electrical connection that may provide power and communication to the circuit board 206 when connected to handheld controller 300. Moreover, instrument specific configuration data, e.g., information indicative of instrument type, specifications, capabilities, etc., stored in the memory chip of circuit board 206 may be transmitted to the microcontroller of handheld controller 300 via electrical connectors 211, 311.

Figure 4B:
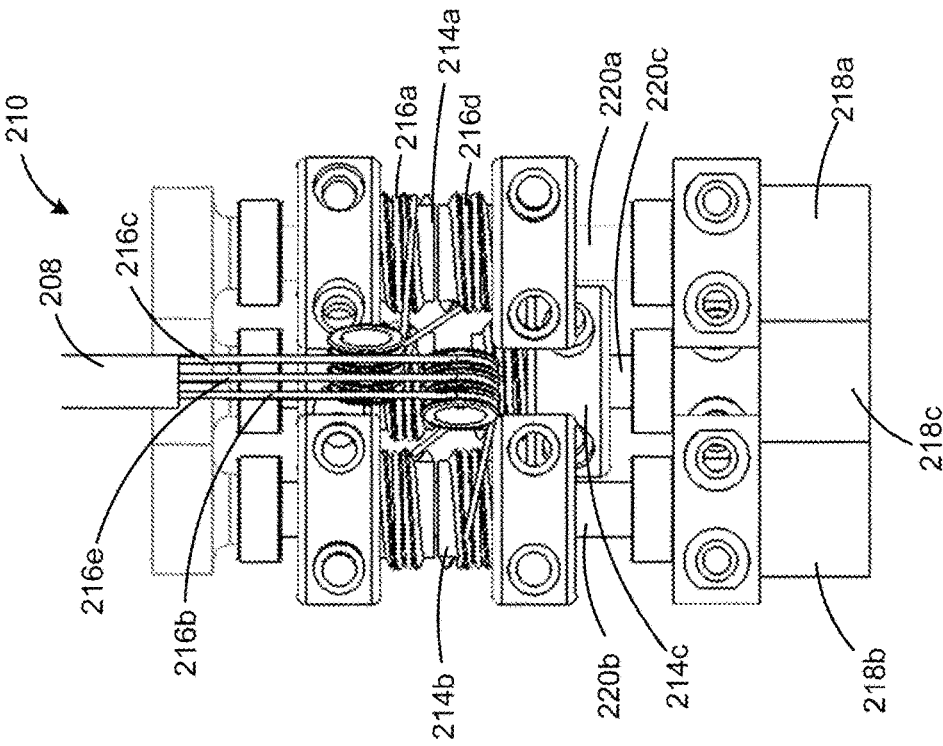
FIGS. 4A and 4B illustrate an exemplary pulley arrangement of the tendon routing system of the interchangeable instrument constructed in accordance with the principles of the present disclosure.
Figure 4A:
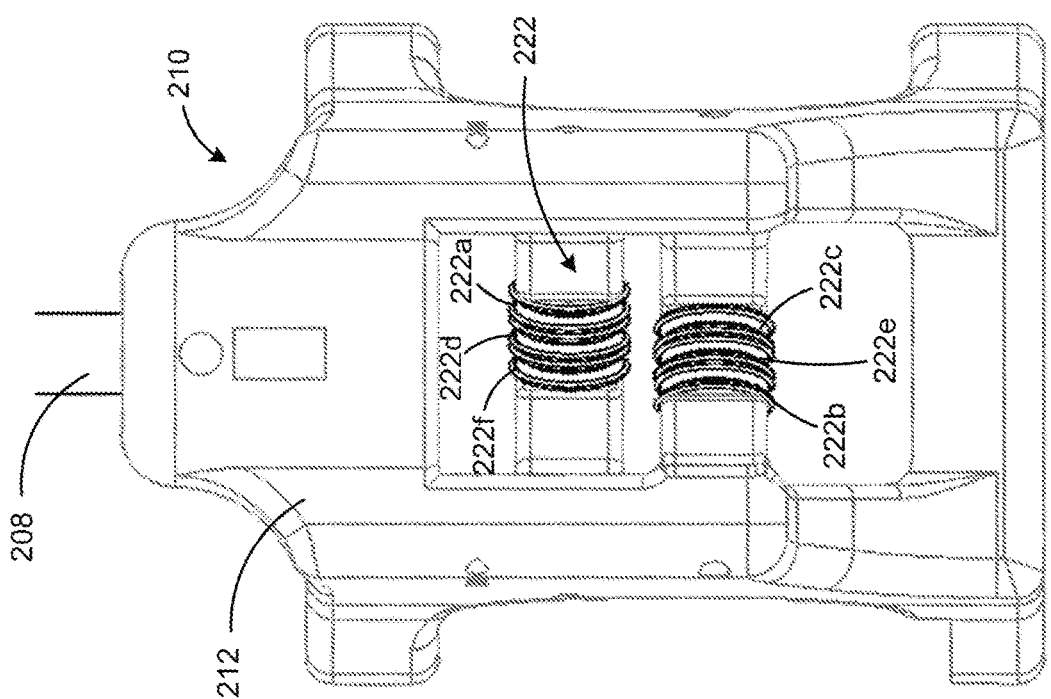

Referring now to FIGS. 4A and 4B, an exemplary pulley arrangement of tendon routing system 210 is provided. Tendon routing system 210 may include a plurality of pulleys 222 configured to redirect tendons 216 from capstans 214 towards and through the respective channel of elongated shaft 208 to end-effector 230. The number of pulleys 222 may correspond to the number of individual tendons 216 of tendon routing system 210, such that each tendon may route through a specific pulley to a specific capstan, where it terminates maintain tension to thereby avoid entanglement within elongated shaft 208. For example, as shown in FIG. 4A, for an interchangeable instrument actuatable in three degrees of freedom, tendon routing system 210 may include six pulleys, e.g., pulleys 222a, 222b, 222c, 222d, 222e, 222f, each pulley independently configured to rotate about its respective axis and to redirect a single tendon from the respective capstan through elongated shaft 208.

Moreover, as shown in FIG. 4B, an interchangeable instrument actuatable in three degrees of freedom may include independently rotatable capstans 214a, 214b, 214c, and each pair of capstans of capstans 214a, 214b, 214c may be coupled to a pair of tendons. For example, the pair of capstans of capstan 214a (for controlling actuation of the end-effector in the pitch degree of freedom) may be coupled to the proximal ends of the pair of tendons comprising tendons 216a, 216d, which may extend from capstan 214a towards and around pulleys 222a, 222d, respectively, to be redirected through one or more respective channels of elongated shaft 208. The pair of capstans of capstan 214b (for controlling actuation of the end-effector in the yaw degree of freedom) may be coupled to the proximal ends of the pair of tendons comprising tendons 216b, 216e, which may extend from capstan 214b towards and around pulleys 222b, 222e, respectively, to be redirected through one or more respective channels of elongated shaft 208. The pair of capstans of capstan 214c (for controlling actuation of the end-effector in the open/close degree of freedom) may be coupled to the proximal ends of the pair of tendons comprising tendons 216c, 216f, which may extend from capstan 214c towards and around pulleys 222c, 222f, respectively, to be redirected through one or more respective channels of elongated shaft 208. As shown in FIG. 4B, capstans 214a, 214b, 214c may be coupled to instrument couplers 218a, 218b, 218c, respectively, via longitudinal shafts 220a, 220b, 220c, respectively, such that rotation of capstans 214a, 214b, 214c is driven by rotation of instrument couplers 218a, 218b, 218c. All interchangeable instruments may have the same coupling system, allowing for interchangeability. However, interchangeable instruments actuatable in only two degrees of freedom may not include a third capstan/instrument coupler.

As shown in FIG. 4A, the pulleys of tendon routing system 210 may be arranged in a manner to minimize the size of the components of tendon routing system 210 within housing 201, while preserving dexterity of the end-effector, thereby providing an overall smaller handheld surgical system. For example, the pulleys may be divided into two sets of pulleys, wherein each set of pulleys has its own axis of rotation, offset from the other. As shown in FIG. 4A, pulleys 222a, 222d, 222f may be arranged to share a first axis of rotation, and pulleys 222b, 222e, 222c may be arranged to share a separate second axis of rotation offset from the first axis of rotation. Moreover, the first and second axes of rotation may be angled relative to each other (FIGS. 3C and 3D), e.g., to align the individual pulleys towards the associated capstans, to thereby facilitate redirecting of the respective tendons from the capstans to elongated shaft 208. For example, as shown in FIG. 4A, pulleys 222a, 222d, 222f may be aligned towards capstans 214a, 214c to thereby receive tendons 216a, 216d from capstan 214a and tendon 216f from capstan 214c, and pulleys 222b, 222e, 222c may be aligned towards capstans 214b, 214c to thereby receive tendons 216b, 216e from capstan 214b and tendon 216c from capstan 214c. A pulley may be aligned with a capstan in that the outer tendon-engaging surface of the pulley is directed towards the capstan.

Referring now to FIGS. 5A to 5D, an exemplary end-effector of an interchangeable instrument actuatable in three degrees of freedom is provided. For example, end-effector 230 may be, e.g., a grasper, scissor, dissector, etc., having one or two movable jaws configured to move toward/away from each other, e.g., in the open/close degree of freedom. Accordingly, end-effector 230 may include first jaw 232 rotatably coupled to second jaw 232 via pivot point 240. As will be understood by a person having ordinary skill in the art, first and second jaws 232, 234 may be blunt graspers as shown in FIG. 5A to 5D, or alternatively, may comprise sharp blades for cutting/dissecting tissue.

Figure 5A:
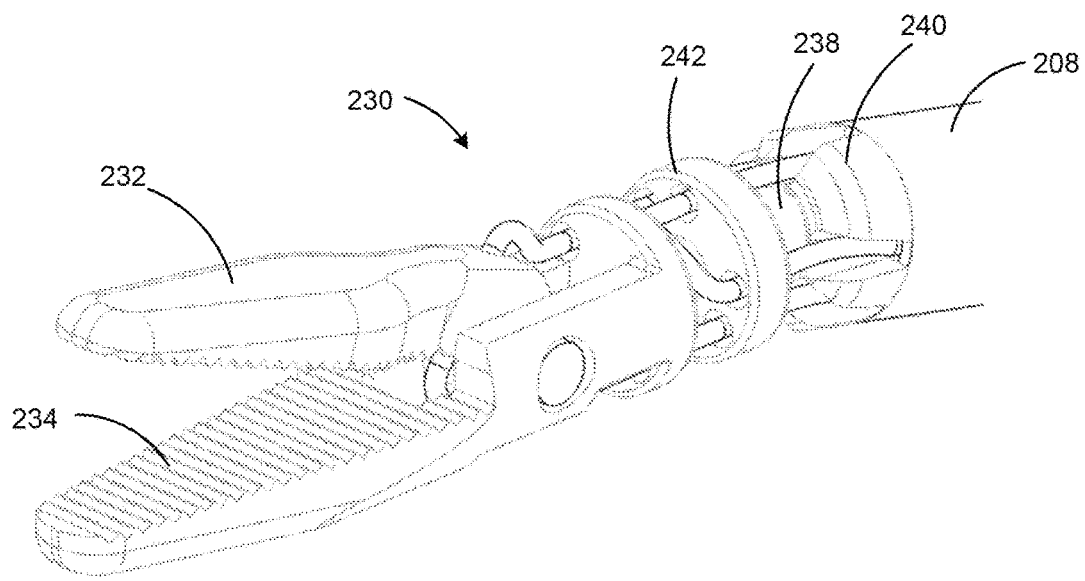
FIGS. 5A to 5D illustrate an exemplary end-effector of the interchangeable instrument constructed in accordance with the principles of the present disclosure.

As shown in FIG. 5A, end-effector 230 may be rotatably coupled to the distal end of elongated shaft 208 via, e.g., a spherical ball joint, thereby permitting rotation of end-effector 230 in two degrees of freedom, e.g., pitch and yaw, relative to elongated shaft 208. For example, end-effector 230 may comprise ball 238 and the distal end of elongated shaft 208 may comprise a ball joint base, e.g., socket 240, configured to rotatably receive ball 238, to thereby form the ball joint as described in U.S. Patent App. Pub. No. 2023/0068155 to Stoyanov, the entire contents of which are incorporated herein by reference. Accordingly, the ball joint may permit a combined actuation of end-effector 230 in both pitch and yaw degrees of freedom simultaneously, e.g., by rotating both capstans 214a, 214b simultaneously.

Figure 5B:
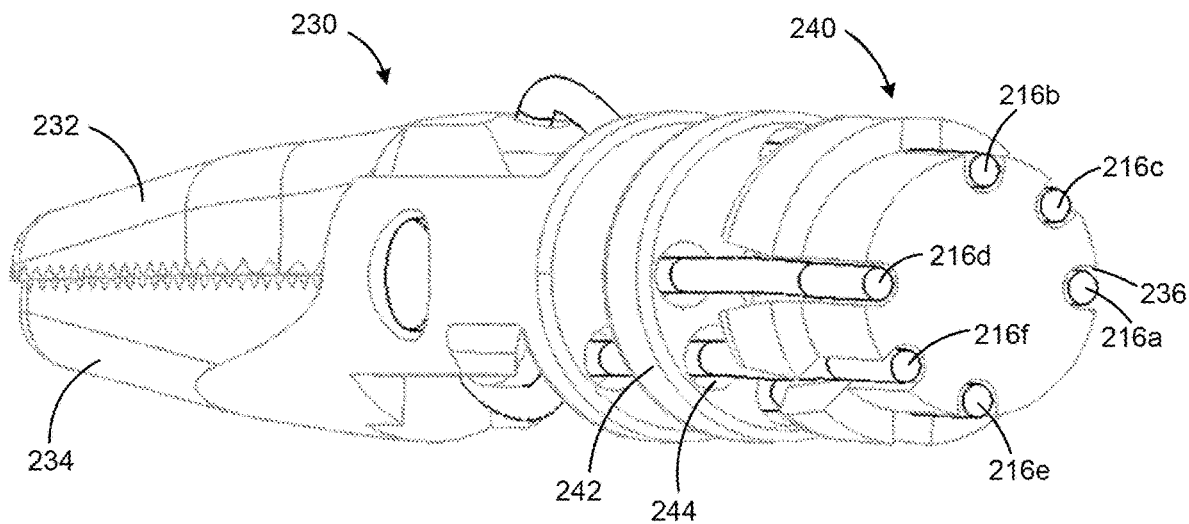

As shown in FIG. 5B, socket 240 may include a plurality of channels 236, each individual channel sized and shaped to slidably receive a single tendon therethrough to thereby provide a path for tendons to route from the instrument tip through the spherical joint to the tendon routing system. For example, channels 236 may comprise a series of angled through holes sized and shaped to provide space and the movement of each tendon at the termination points as the instrument tip moves responsive to antagonistic motion. Channels 236 may extend throughout the entire length of elongated shaft 208, or alternatively may only extend through socket 240, such that all the tendons extend through a common lumen of elongated shaft 208 until they are routed through respective channels 236 of socket 240. In addition, end-effector 230 further may include ring 242 disposed adjacent/distal to the ball joint, ring 242 having channels 244 sized and shaped to slidably receive a single tendon therethrough. Accordingly, ring 242 may guide the tendons from socket 240 towards their respective termination points along end-effector 230, thereby improving stability of the tendons.

Figure 5D:
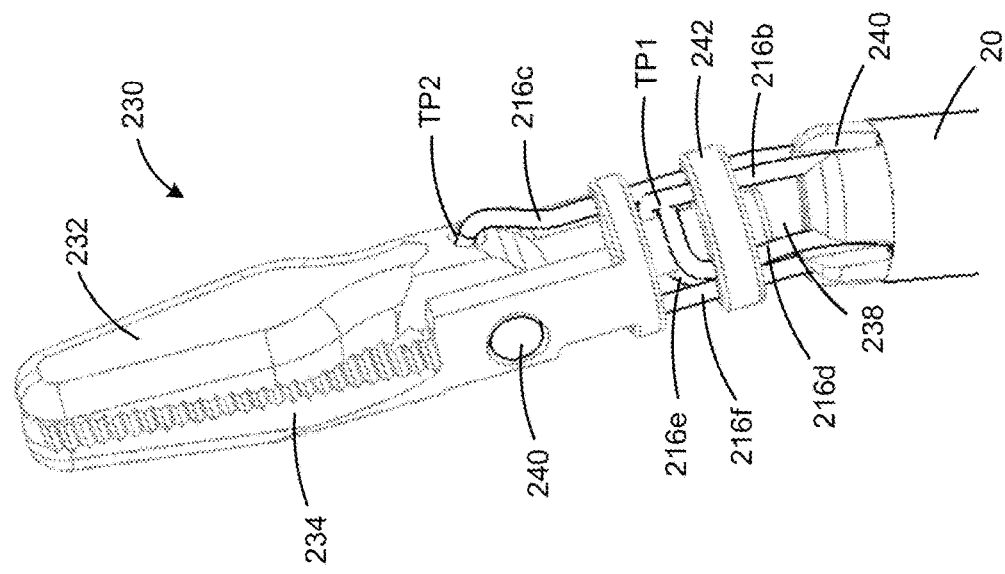
Figure 5C:
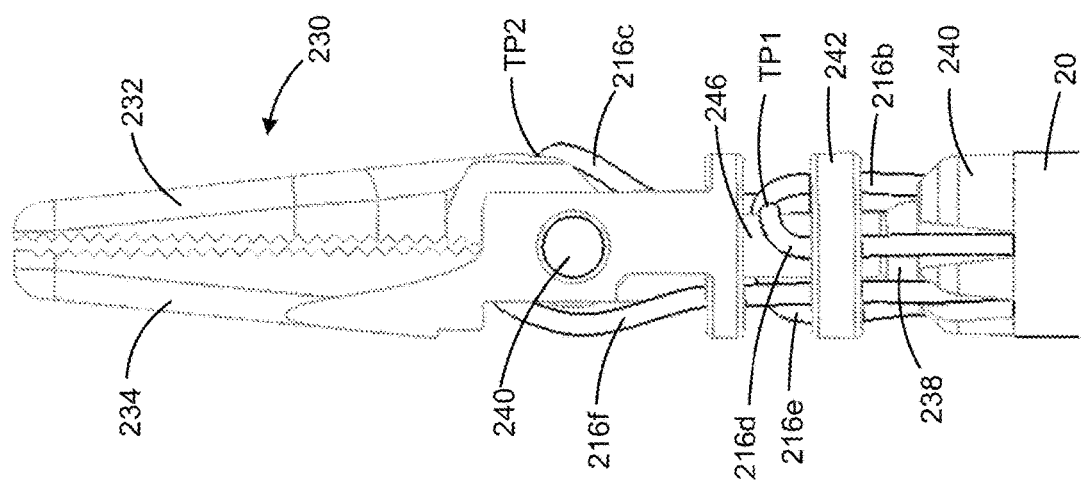
Figure 6A:
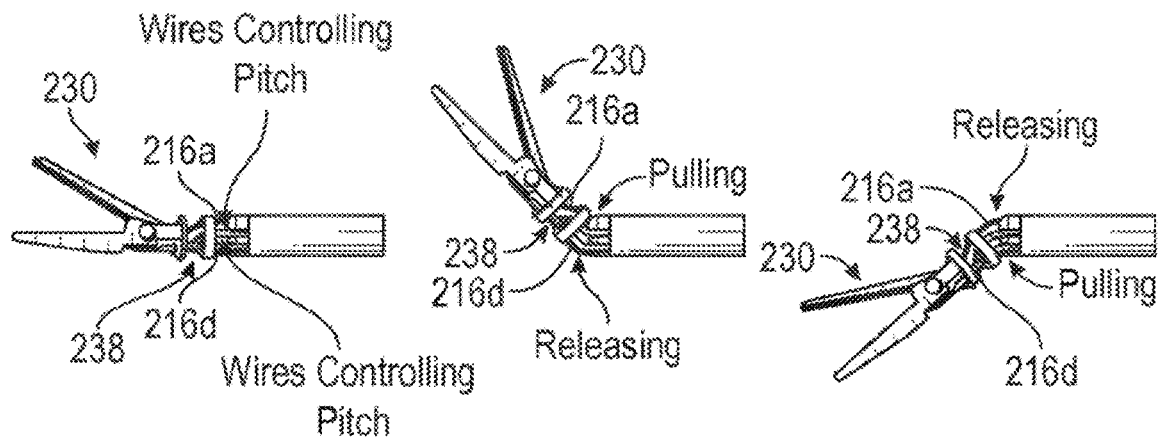
FIGS. 6A to 6C illustrate the degrees of freedom of actuation of the end-effector of the interchangeable instrument in accordance with the principles of the present disclosure.

In addition, the distal ends of each pair of antagonistic tendons may terminate at an end-effector link of end-effector 230, e.g., coupled to opposite sides of the end-effector link, such that the antagonistic pulling/releasing of the pair of tendons permits controllable rotation of the end-effector link about a corresponding axis of rotation by pulling/pushing the end-effector link in a direction along the degree of freedom to thereby achieve the intended movement of end-effector 230 in the corresponding degree of freedom. Accordingly, when tension is applied to the tendons from both sides, antagonistic motion may be performed. As shown in FIGS. 5C and 5D, the distal ends of a first pair of antagonistic tendons, e.g., tendons 216a (not shown), 216d, may be coupled to opposite sides of end-effector link 246 at termination point TP1, e.g., via glue, crimps, or knots, such that the antagonistic pulling/releasing of tendons 216a, 216d will rotate end-effector link 246, and accordingly all of the components of end-effector 230 distal to link 246, about a pitch-axis in the pitch degree of freedom about ball joint 238, as shown in FIG. 6A. Considering termination point TP1 as the middle, the antagonistic motion may be defined as the pulling of tendon 216a from one side, while simultaneously pushing/releasing tendon 216d from the other side of termination, allowing for rotation in the direction of pulling and pushing of the spherical joint. Ring 242 may be coupled to and surround end-effector shaft link 246, such that ring 242 also rotates along with link 246 responsive to the antagonistic pulling/releasing of tendons 216a, 216d, as shown in FIG. 5D.

Figure 6B:
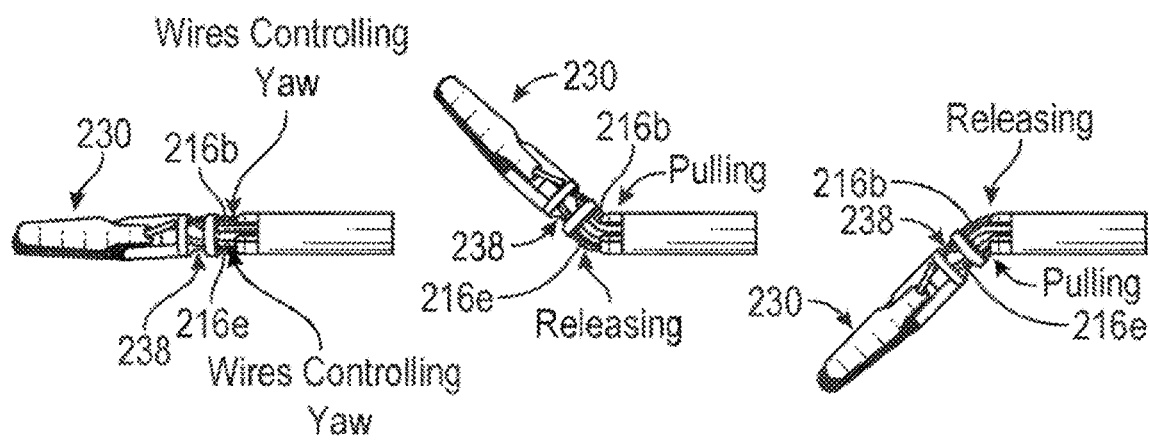
Figure 6C:
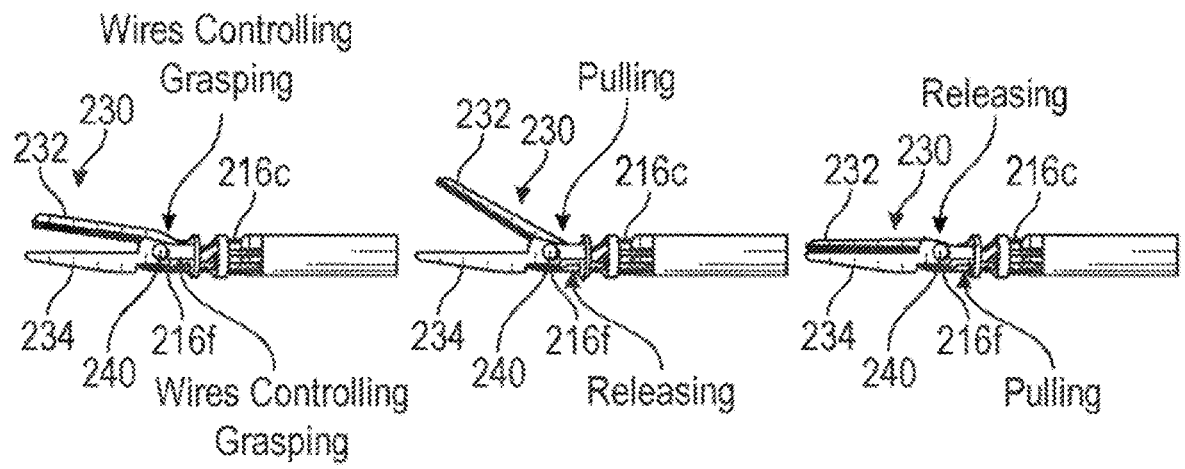
Figure 7:
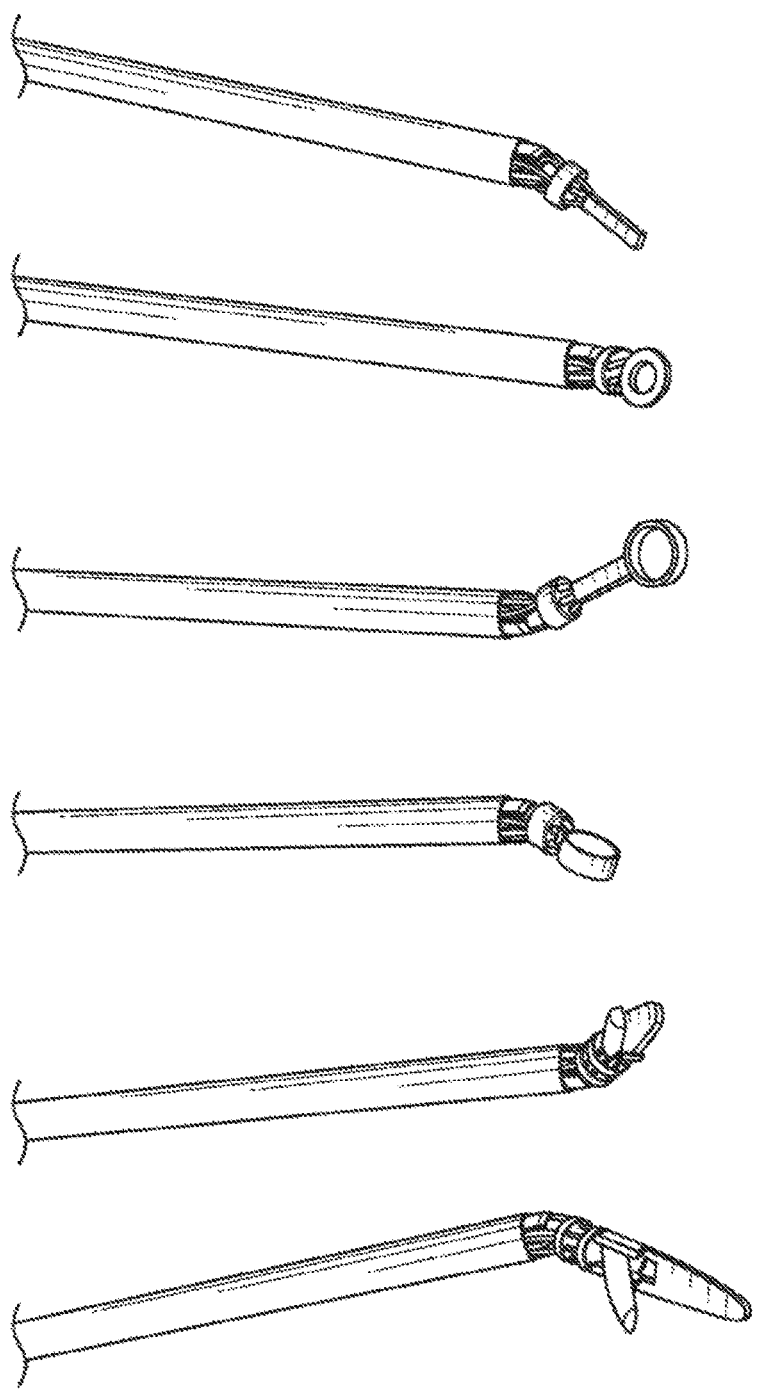
FIG. 7 illustrates alternative exemplary end-effectors of various interchangeable instruments.

Similarly, the distal ends of a second pair of antagonistic tendons, e.g., tendons 216b, 216e, may be coupled to opposite sides of end-effector link 246 at termination point TP1, e.g., in between the connection points of tendons 216a, 216d to link 246, such that the antagonistic pulling/releasing of tendons 216b, 216e will rotate end-effector link 246, and accordingly all of the components of end-effector 230 distal to link 246, about a yaw-axis in the yaw degree of freedom about the ball joint 238, as shown in FIG. 6B. The distal ends of a third pair of antagonistic tendons, e.g., tendons 216c, 216f, may be coupled to opposite sides of first jaw 232 at termination point TP2, such that the antagonistic pulling/releasing of tendons 216c, 216f will rotate first jaw 232 about pivot point 240 relative to second jaw 234, thereby actuating end-effector 230 in the open/close degree of freedom, as shown in FIG. 6C. For example, tendons 216c, 216f may be coupled to first jaw 232 via looping, crimping, gluing, etc. As described above, various interchangeable surgical instruments having various end-effectors may be selected for coupling with handheld controller 300 to allow for better and more precise tissue removal and manipulation, depending on the surgical procedure. For example, FIG. 7 illustrates various end-effectors from left to right: long grasper, short grasper, ring-curette, long ring-curette, spoon curette, and dissector. The various end-effectors further may include a suction tip, an endoscope, and/or needle holder.

Referring now to FIGS. 8A to 8D, an exemplary handheld controller is provided. Handheld controller 300 is sized and shaped to be held and controlled by a user's hand, and may include connection portion 301 having coupling interface 303 for removeably coupling to coupling interface 203 of interchangeable instrument 200, and handle portion 302 configured to be ergonomically held by the user's hand. Preferably, handheld controller 300 weighs no more than, e.g., 200 grams. Handheld controller 300 may comprise of a rigid handle body, four user input interfaces, namely a joystick, a trigger, two buttons, and a movable joystick component that improves the ergonomics of handle controller 300. As shown in FIG. 8D, coupling interface 303 may include electrical connector 311 configured to be electrically connected to electrical connector 211 of interchangeable instrument 200, to thereby transmit electrical signals and power between handheld controller 300 and interchangeable instrument 200. As described in further detail below with regard to FIGS. 9A to 9D, handle portion 302 may be selectively, rotatable coupled to connection portion 301. Alternatively, connection portion 301 and handle portion 302 may be integrally formed, e.g., share a common housing.

Referring again to FIGS. 8A to 8D, handheld controller 300 further may include latch 308 configured to releasably engage with groove 205 of interchangeable instrument 200, to thereby securely lock interchangeable instrument 200 to handheld controller 300. Accordingly, latch 308 may be include an interface configured to be pressed/moved by the user to transition latch 308 between a locked state and unlocked state. For example, latch 308 may be moved to the unlocked state to permit coupling of interchangeable instrument 200 to handheld controller 300, then released/moved to the locked state where latch 308 releasably engages with groove 205 of interchangeable instrument 200 to securely lock interchangeable instrument 200 to handheld controller 300. Accordingly, latch 308 may be manually actuated in order to couple or decouple interchangeable instrument 200 from handheld controller 300, which may be detected electronically via a digital switch. As will be understood by a person having ordinary skill in the art, the latch may be disposed on the interchangeable instrument, and the groove configured to releasably engage with the latch may be disposed on the connection portion of the handheld controller.

Moreover, handheld controller 300 may include a motor pack, e.g., one or more DC motors 305, configured to cause rotation of capstans 214 responsive to user input received at handheld controller 300 when interchangeable instrument 200 is coupled to handheld controller 300. For example, motors 305 may include three motors, each motor operatively coupled to a respective controller coupler, e.g., controller couplers 310a, 310b, 310c, via respective motor shafts, and configured to actuate rotation of the respective controller coupler. Controller couplers 310a, 310b, 310c may be configured to releasably engage with instrument couplers 218a, 218b, 218c of interchangeable instrument 200 when interchangeable instrument 200 is coupled to handheld controller 300, such that rotary motion may be transmitted from motors 305 to capstans 214a, 214b, 214c via controller couplers 310a, 310b, 310c and instrument couplers 218a, 218b, 218c, respectively.

In addition, handheld controller 300 may include a plurality of interfaces operatively coupled to one or more motors 305, each interface configured to receive user input and generate one or more signals for causing one or more motors 305 to actuate end-effector 230 in one or more degrees of freedom, as described in further detail below. For example, handheld controller 300 may include joystick 304 configured to be moved by a user, e.g., left/right, up/down, or a combination thereof, for actuating end-effector 230 in the pitch and/or yaw degrees of freedom. For example, joystick 304 may function similarly to many handheld gaming controllers. Accordingly, upon actuation of joystick 304, e.g., up/down, handheld controller 300 may generate a signal to actuate motor 305 to cause rotation of controller couplers 310a, which causes rotation of instrument coupler 218a releasably coupled thereto, and accordingly capstan 214a, which causes the antagonistic pulling/releasing of tendons 216a, 216d, to thereby move end-effector 230 in the pitch degree of freedom. Additionally, upon actuation of joystick 304, e.g., left/right, handheld controller 300 may generate a signal to actuate motor 305 to cause rotation of controller couplers 310b, which causes rotation of instrument coupler 218b releasably coupled thereto, and accordingly capstan 214b, which causes the antagonistic pulling/releasing of tendons 216b, 216e, to thereby move end-effector 230 in the yaw degree of freedom. Preferably, joystick 304 is disposed on handle portion 302 in a position such that it is movable via the user's thumb, which as described above, may be adjusted to accommodate comfort of the user.

In addition, handheld controller 300 may include trigger 306 configured to be pulled by the user for actuating end-effector 230 in the open/close degree of freedom. Accordingly, upon actuation of trigger 306, handheld controller 300 may generate a signal to actuate motor 305 to cause rotation of controller couplers 310c, which causes rotation of instrument coupler 218c releasably coupled thereto, and accordingly capstan 214c, which causes the antagonistic pulling/releasing of tendons 216c, 216f, to thereby move end-effector 230 in the open/close degree of freedom. In some embodiments, handheld controller 300 may include an additional interface that, when pressed by the user, generates a signal that causes capstans 214 to return to their respective neutral orientations, and accordingly, causes end-effector 230 to return to a straight, unactuated configuration, neutral in all degrees of freedom.

Referring now to FIGS. 9A and 9B connection portion 301 of handheld controller 300 is provided. Motor pack 305 holding all the motors therein may provide translational compliance along an axis parallel to each motor axis to facilitate self-alignment of controller couplers 310a, 310b, 310c with instrument couplers 218a, 218b, 218c, as described in further detail below with regard to FIGS. 10A to 10E. For example, as shown in FIGS. 9A and 9B, compliant motor pack 305 may be coupled to spring 320 configured to apply a resistive spring force distally to motor pack 305 to return spring 320 to its natural length, thereby biasing motor pack 305 outward in the configuration illustrated in FIG. 9A. In some embodiments, each individual motor may be coupled to a respective spring, such that each individual motor may independently provide translational compliance along its respective motor axis to facilitate self-alignment of each individual controller coupler with the corresponding instrument coupler.

FIG. 9A shows compliant motor pack 305 in its fully extended position with spring 320 at its natural length. Accordingly, upon application of a force proximally to motor pack 305, spring 320 may compress to permit motor pack 305 to move inward along an axis parallel to the motor axes to the configuration illustrated in FIG. 9B, which shows compliant motor pack 305 in its retracted position. The resistive force provided by spring 320 facilitates engagement between instrument couplers 218 and controller couplers 310, as described in further detail below. Moreover, as shown in FIGS. 9A and 9B, proximal end 316 of connection portion 301 may comprise a geometry sized and shaped to securely interlock with a corresponding geometry at the distal end of handle portion 302 at select angular increments. For example, proximal end 316 may comprise a hirth gear, thereby forming a hirth joint between connection portion 301 and handle portion 302. Alternatively, proximal end 316 may form a bevel joint between connection portion 301 and handle portion 302.

Figure 9D:
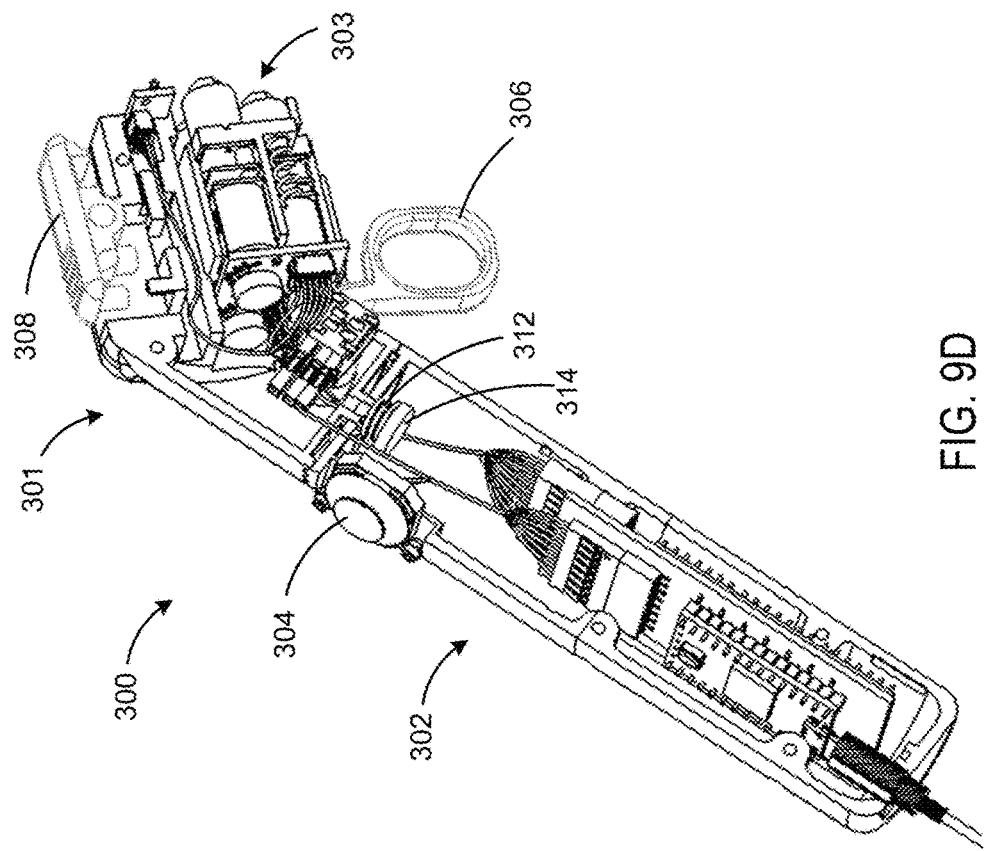
FIGS. 9C and 9D illustrate the internal components of an exemplary handle portion of the handheld controller having a moveable joystick component constructed in accordance with the principles of the present disclosure.
Figure 9C:
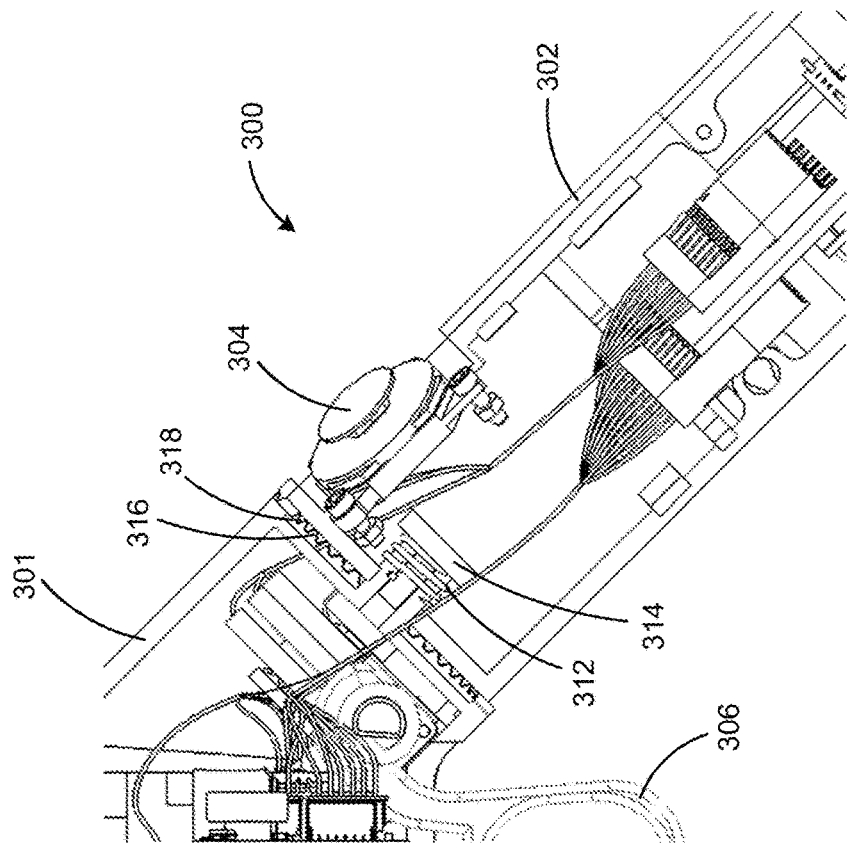

Referring now to FIGS. 9C and 9D handle portion 302 of handheld controller 300 is provided. As shown in FIG. 9C, distal end 318 of handle portion 302 may comprise a geometry sized and shaped to securely interlock with a corresponding geometry at proximal end 316 of connection portion 301 at select angular increments. For example, distal end 318 may comprise a hirth gear, thereby forming a hirth joint between connection portion 301 and handle portion 302. Moreover, handle portion 302 may include compression spring 312 operatively coupled to connection portion 301, and configured to apply a spring force to handle portion 302 to thereby bias handle portion 302 towards connection portion 301. Handle portion 302 further may include spring cap 314 coupled to a proximal end of spring 312, and configured to provide a stable compression position for spring 312. Accordingly, handle portion 302 may be pulled proximally relative to connection portion 301 to thereby disengage the hirth gears at distal end 318 and proximal end 316, and further rotated relative to connection portion 301 to selectively adjust the angular position of handle portion 302, and accordingly joystick 304, relative to connection portion 301. Spring cap 314 further may prevent over-pulling of handle portion 302 relative to connection portion 301. Upon release of handle portion 302, spring 312 will pull handle portion 302 towards connection portion 301, such that the hirth gears at distal end 318 and proximal end 316 are reengaged at the adjusted angular position of handle portion 302 relative to connection portion 301, thereby providing rotational rigidity. Alternatively, distal end 318 may form a bevel joint between connection portion 301 and handle portion 302 via proximal end 316.

Figure 10A:
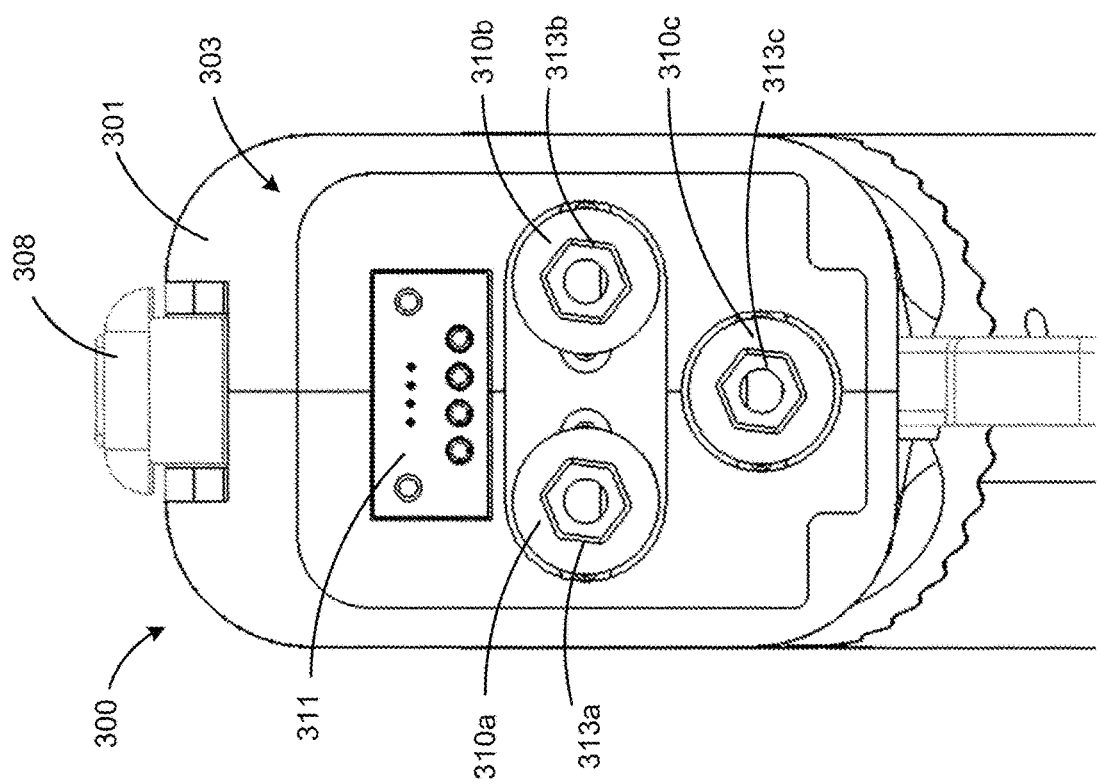
FIGS. 10A to 10E illustrate an exemplary coupling interface of the handheld controller and the interchangeable instrument constructed in accordance with the principles of the present disclosure.
Figure 10A:
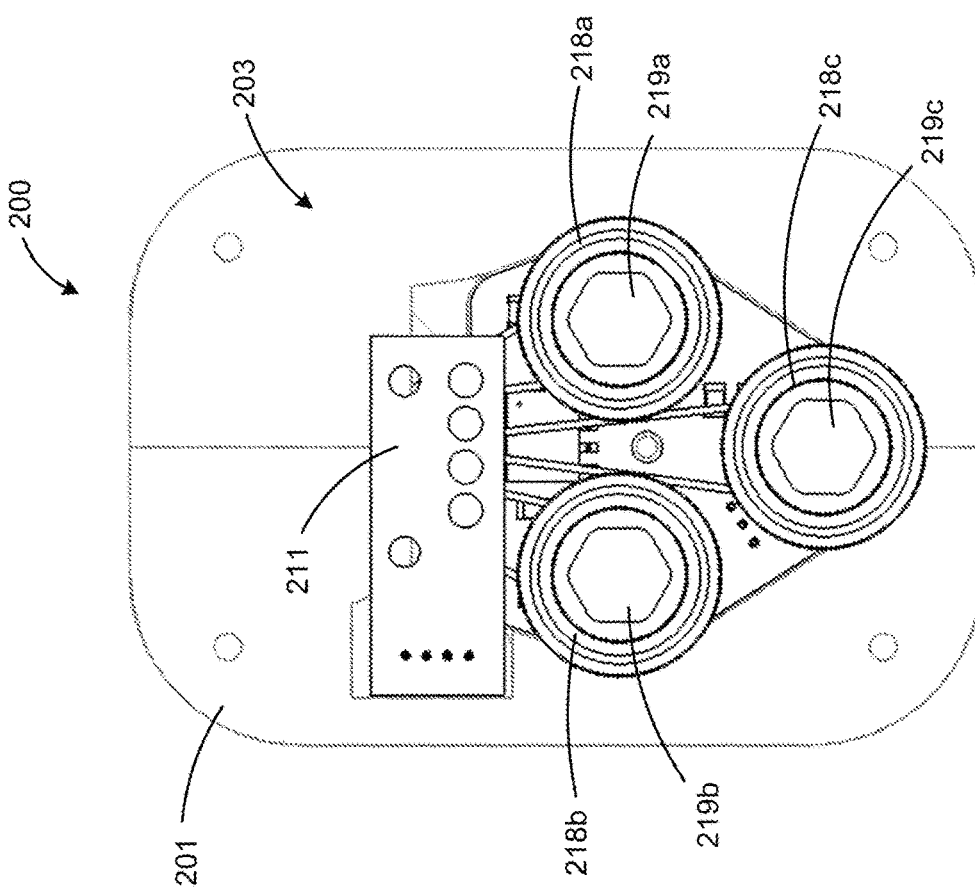

Referring now to FIGS. 10A to 10E, an exemplary coupling interface of the handheld controller and the interchangeable instrument is provided. As shown in FIG. 10A, coupling interface 203 of interchangeable instrument 200 may include electrical connector 211 and instrument couplers 218a, 218b, 218c, each instrument coupler having a groove feature engraved within the body of the instrument coupler, e.g., grooves 219a, 219b, 219c (collectively referred to as grooves 219), respectively, and coupling interface 303 of connection portion 301 of handheld controller 300 may include electrical connector 311 and controller couplers 310a, 310b, 310c, each controller coupler having a boss feature extruding from the both of the controller coupler, e.g., bosses 313a, 313b, 313c (collectively referred to as bosses 313), respectively. As described above, electrical connector 211 is configured to be electrically connected to electrical connector 311, to thereby transmit electrical signals and power between handheld controller 300 and interchangeable instrument 200.

Figure 10B:
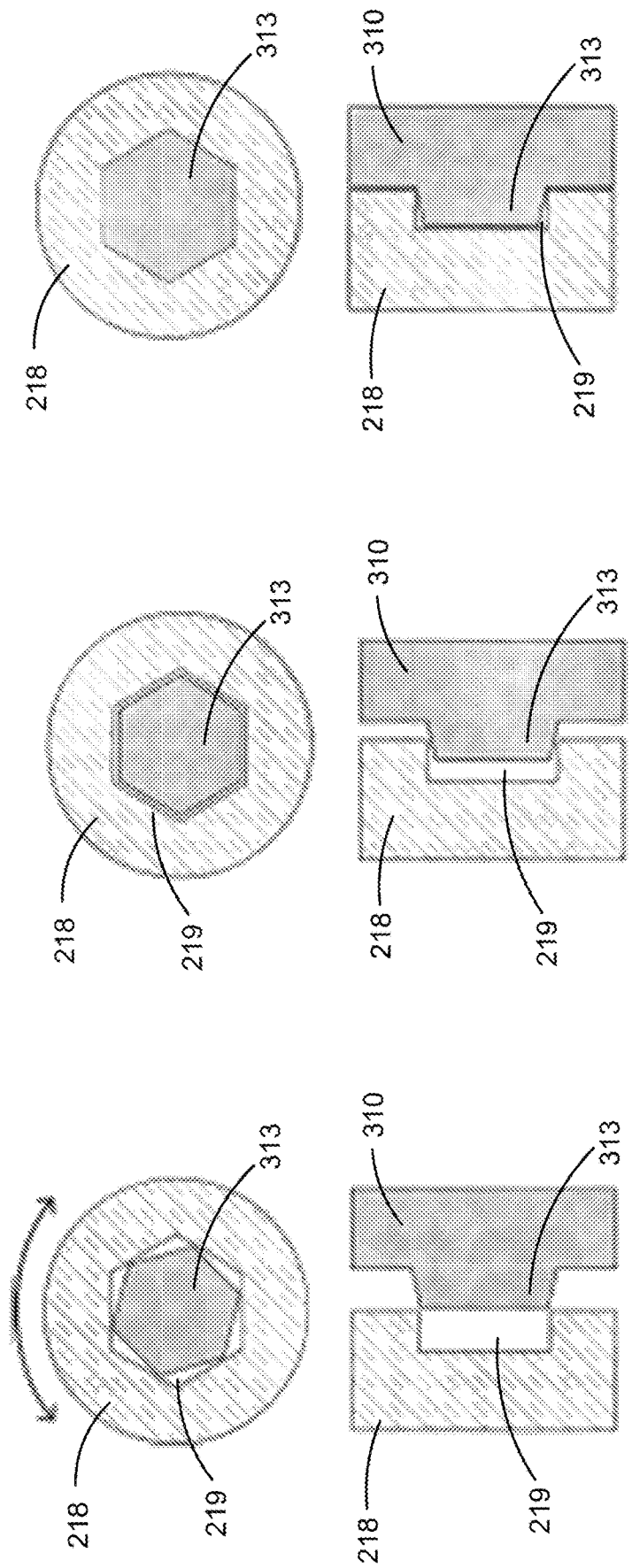

Grooves 219 may be sized and shaped to releasably receive bosses 313, to thereby transmit rotary motion between motors 305 and capstans 214. Moreover, grooves 219 and bosses 313 may be sized and shaped to facilitate self-alignment of bosses 313 with grooves 219. For example, as shown in FIG. 10B, bosses 313 may have a portion comprising a tapered profile, such that the cross sectional area of the tapered portion of bosses 313 decreases in the distal direction from controller coupler 310 towards instrument coupler 218. The taper is designed so that the circumscribed diameter of the tapered portion of bosses 313 is smaller than the inscribed diameter of the full profile of grooves 219, thereby ensuring that bosses 313 and grooves 219 will at least partially engage even at maximum misalignment. Accordingly, the tapered boss and groove features provide the main alignment and structural connection between interchangeable instrument 200 and handheld controller 300. When coupling, these features will be the first to interact, ensuring the alignment between the motor and capstan axis before the instrument and controller couplers interact. In some embodiments, bosses 313 may further include a non-tapered portion, e.g., extending parallel to the longitudinal axis of the boss, following the tapered portion, thereby providing additional surface contact between bosses 313 and grooves 219, which allows for more torque to be transferred from the controller couplers to the instrument couplers, as well as a larger axial difference between the couplers of each degree-of-freedom. Further, grooves 219 and bosses 313 may have corresponding, non-circular geometries, e.g., a profile with multiple lines of symmetry intersecting the axis of rotation, to thereby facilitate transmission of rotary motion between controller coupler 310 and instrument coupler 218. For example, grooves 219 and bosses 313 may have hexagonal profile, as shown in FIG. 10B.

Figure 10C:
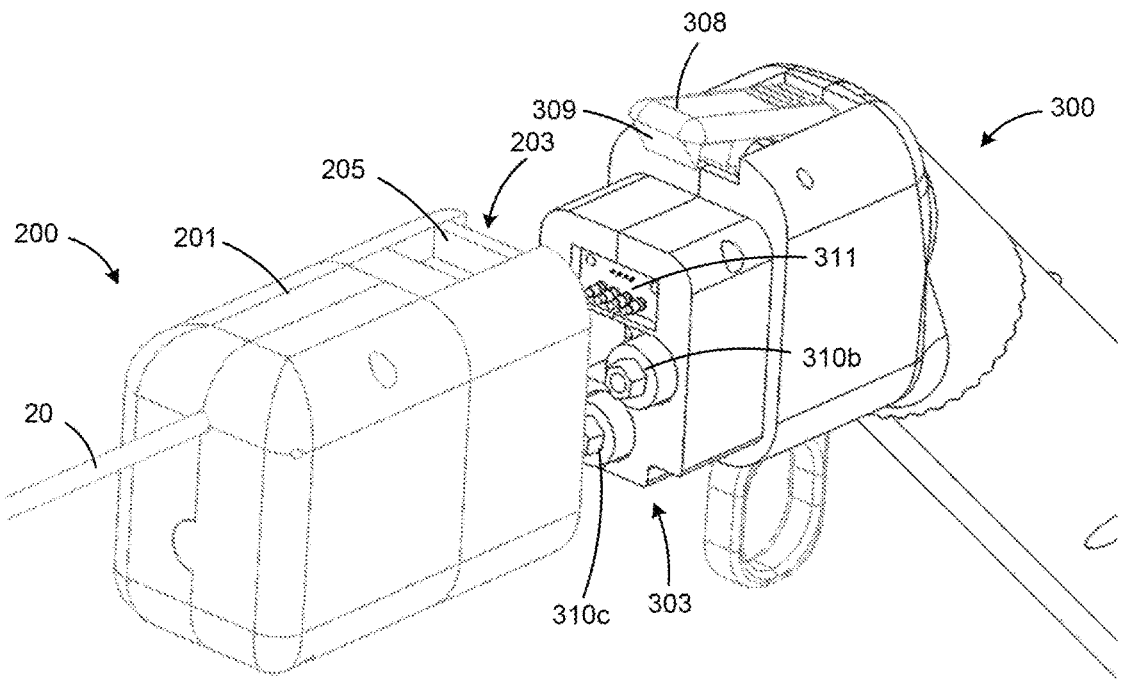
Figure 10D:
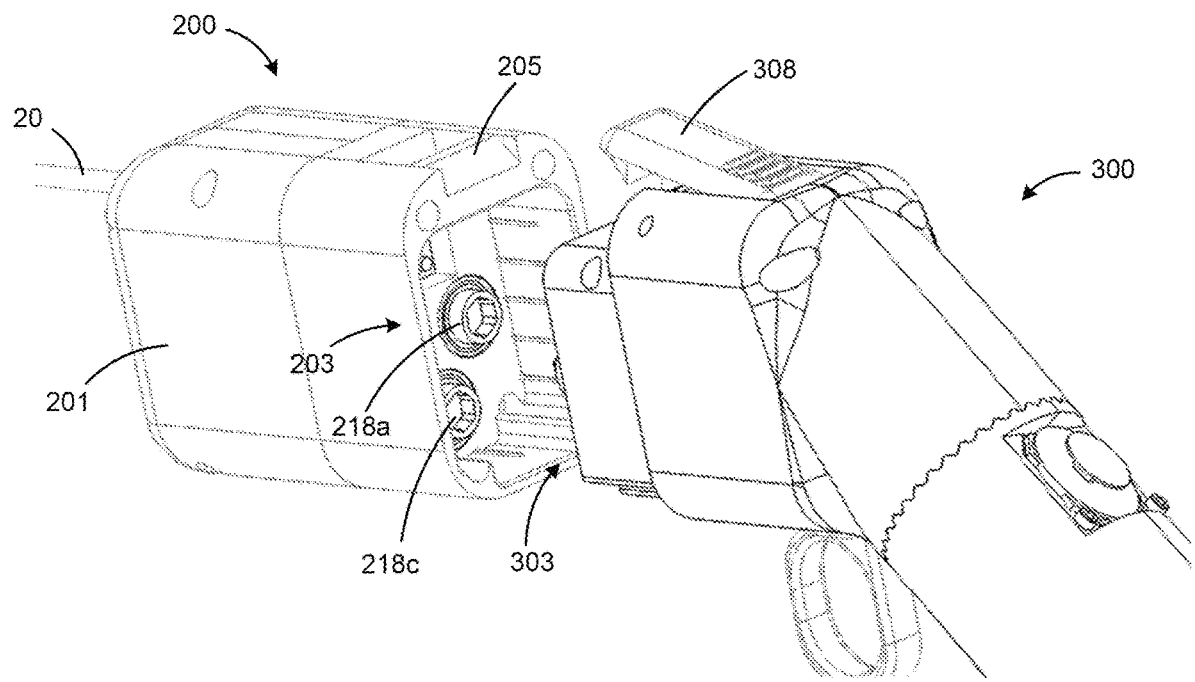
Figure 10E:
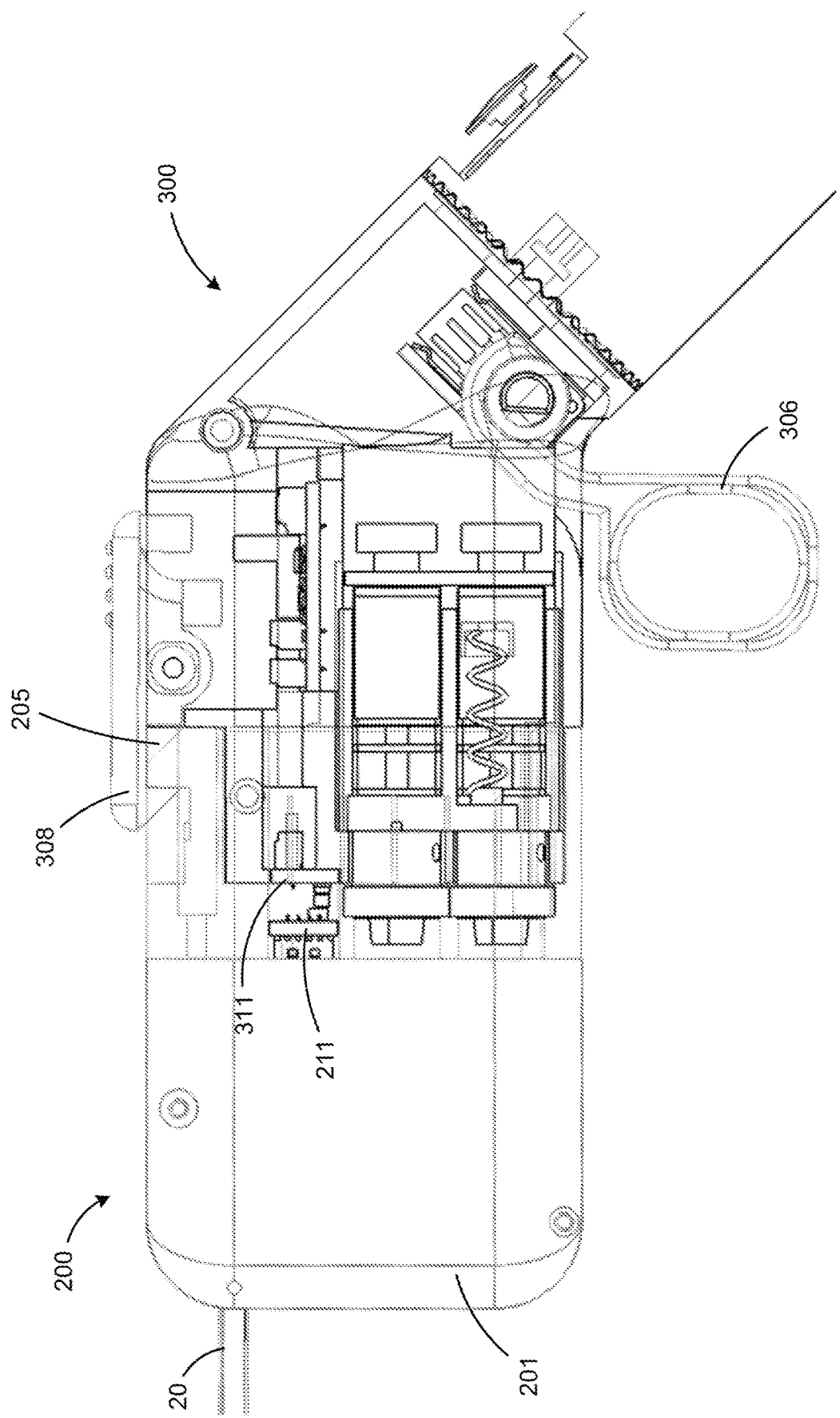

As shown in FIGS. 10C and 10D, handheld controller 300 may be coupled to interchangeable instrument 200 by generally aligning coupling interface 303 with coupling interface 203, and moving connection portion 301 towards housing 201 with latch 308 in its unlocked state until bosses 313 contacts grooves 219. As described above, the tapered portion of bosses 313 will cause bosses 313 to self-align with grooves 218, e.g., by causing controller couplers 310 to rotate until the profiles of each boss 313 are aligned with the profiles of each groove 219. If any of bosses 313 are not aligned with grooves 218 during coupling of coupling interface 203 with coupling interface 303, the force applied to controller couplers 310, and accordingly motor pack 305, by instrument couplers 218 will cause compliant motor pack 305 to be retracted within connection portion 301, e.g., via spring 320 (FIG. 9B), until controller couplers 310 self-align with instrument couplers 218 and bosses 313 are inserted within grooves 219, as shown in FIG. 10E. Additionally, or alternatively, when motor pack 305 is in the retracted position, one or more interfaces, e.g., joystick 304 and/or trigger 306, may be at least slightly moved around by the user to cause motors 305 to slightly rotate controller couplers 310 until bosses 313 are inserted within grooves 219, e.g., via the engagement between the tapered portion of bosses 313 and grooves 219. Latch 308 may then be returned to its locked state to securely lock interchangeable instrument 200 to handheld controller 300.

Figure 11:
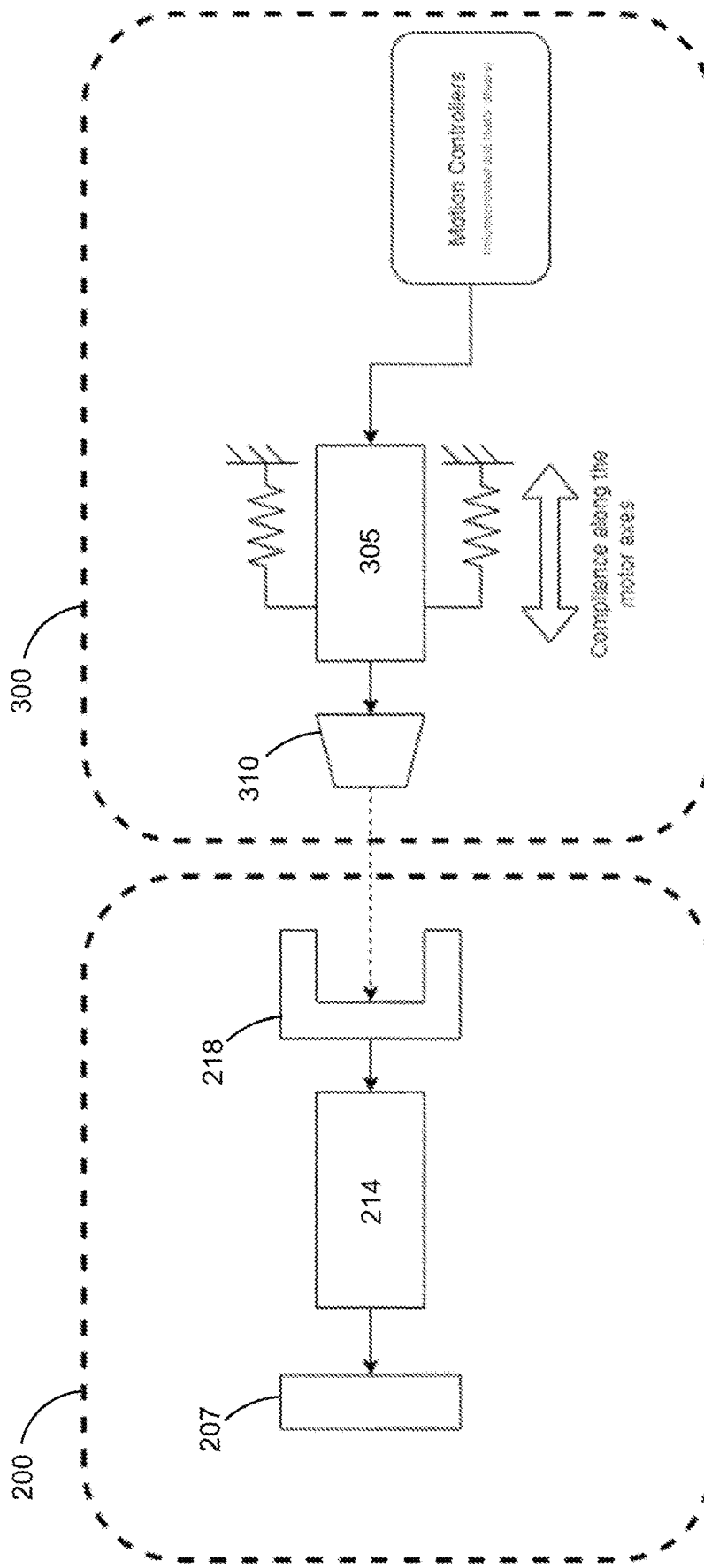
FIG. 11 is a schematic of the coupling interface of the handheld controller and the interchangeable instrument.
Figure 12A:
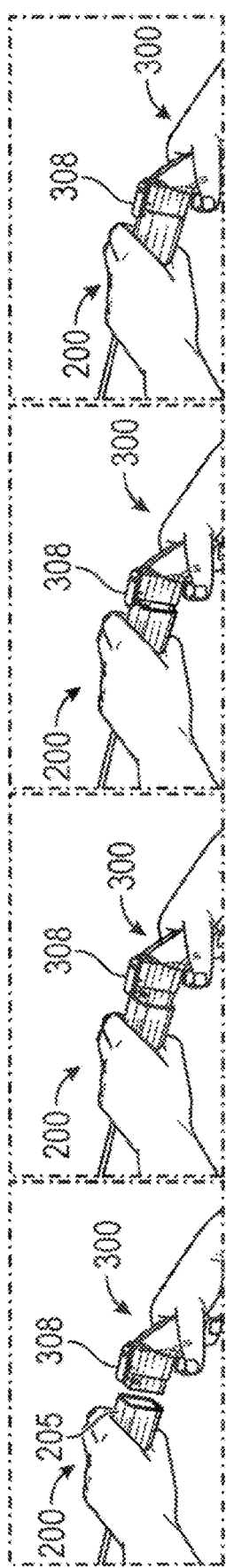
FIGS. 12A and 12B illustrate coupling and decoupling of the handheld controller and the interchangeable instrument in accordance with the principles of the present disclosure.
Figure 12B:
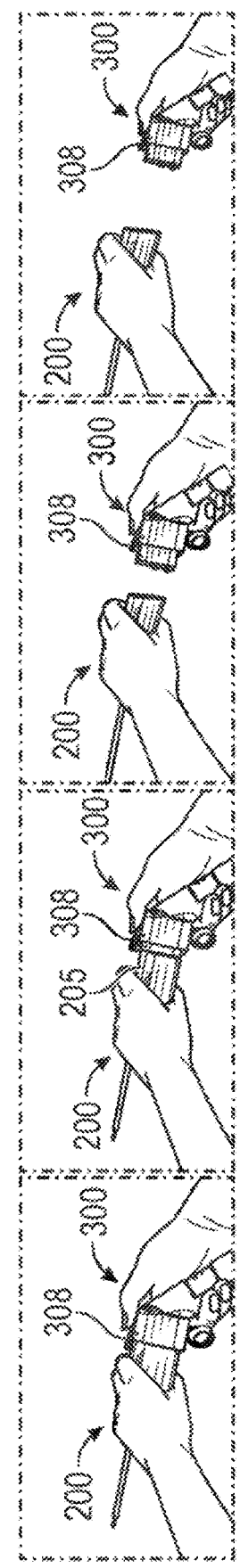

FIG. 11 illustrates the transmission chain of handheld surgical system 100 when handheld controller 300 is being coupled to interchangeable instrument 200. For example, as described above, the coupling procedure where the instrument and handheld controller couplers are not aligned is as follows. Interchangeable instrument 200 and handheld controller 300 are brought together and housing 201 and connection portion 301 are rigidly attached via bosses 313 and grooves 219, and secured together via latch 308, as shown in FIG. 12A. As instrument couplers 218 and controller couplers 310 are not aligned, motor pack 305 is moved back towards the base of connection portion 301 to the point of contact between instrument couplers 218 and controller couplers 310. Moving the actuators in a reciprocal motion combined with the axial force applied from the compliance of motor pack 305 will align instrument couplers 218 and controller couplers 310 and fully engage instrument couplers 218 with controller couplers 310. Moreover, the engagement of instrument couplers 218 and controller couplers 310 may be verified via capstan position resolvers 207. To decouple interchangeable instrument 200 from handheld control 300, latch 308 may be moved to its unlocked state, and a force may be applied to handheld controller 300 to disengage coupling interface 303 from coupling interface 203 and release interchangeable instrument 200 from handheld control 300, as shown in FIG. 12B. As shown in FIG. 11, motion controllers, e.g., a microcontroller and motor drivers, operatively coupled to motor pack 205 for controlling operation of handheld surgical system 100 may be disposed within handheld controller 300.

Figure 13:
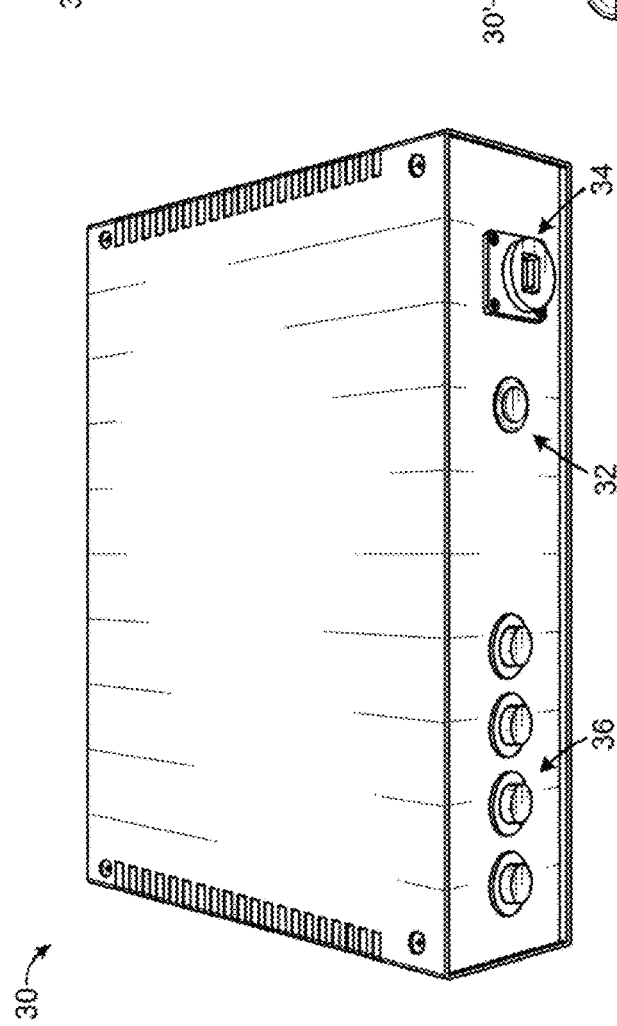
FIG. 13 illustrates an exemplary console of the handheld surgical system constructed in accordance with the principles of the present disclosure.

Referring now to FIG. 13, an exemplary console is provided. Console 30 may be a separate unit and may be operatively coupled to handheld surgical system 100 via cable 20 for providing some primary and additional secondary functionality to system 100. For example, console 30 may provide power to system 100, as well as accurate control of the dexterous end-effector of the attached interchangeable instrument. Console 30 may incorporate a power supply and a single-board computer that allows for user input and tuning. As shown in FIG. 13, console 30 may include power button 32 for powering on and off console 30, an input/output port 34 for providing power and communication to handheld controller 300, and a power inlet connector that provides power to console 30 from the building power supply. Additionally, console 30 may incorporate a series of four push buttons 36 and scrolls for interfacing with the handheld controller directly. The push buttons may have individual functions, e.g., quick settings that may be accessible from the console, such as emergency stop or joints enable/disable. Moreover, console 30 may receive information from handheld controller 300 such as the status of handheld controller 300 or the connected instrument and additionally raise errors through visual and auditory alarms.

Figure 14A:
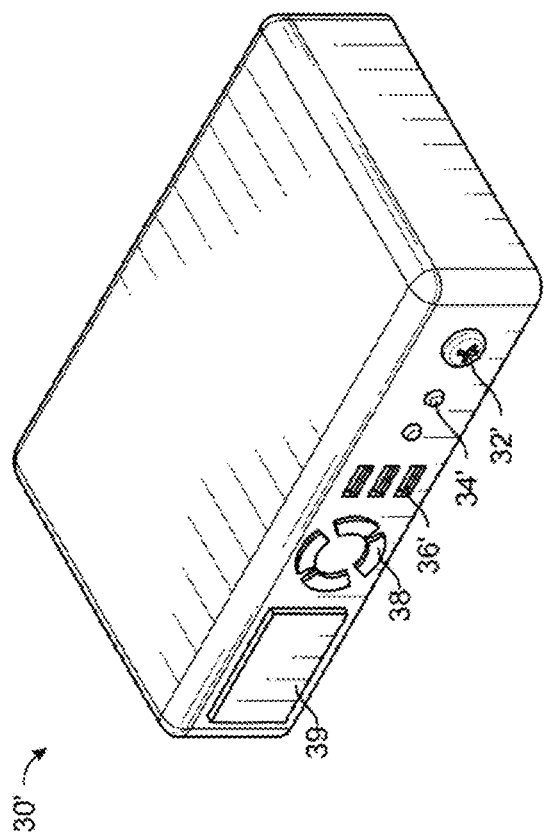
FIGS. 14A and 14B illustrate an alternative exemplary console of the handheld surgical system constructed in accordance with the principles of the present disclosure.
Figure 14B:
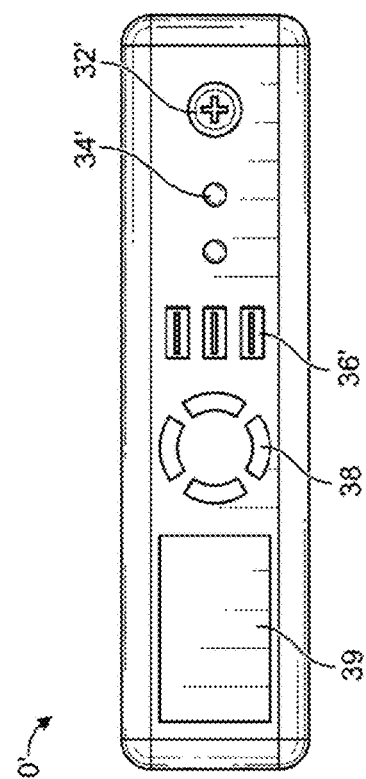

Referring to FIGS. 14A and 14B, an alternative exemplary console is provided. Console 30' may be constructed similar to console 30, with similar components having like-prime reference numerals. For example, power button 32', input/output port 34', and push buttons 36' correspond with power button 32, input/output port 34, and push buttons 36. Console 30' differs from console 30 in that input/output port 34' may incorporate multi-connector ports. In addition, console 30' further may include speed control interface 38 for tuning the maximum speed with which the instrument tip can travel or in general. As shown in FIGS. 14A and 14B, console 30' further may include display 39, e.g., an LCD screen, for displaying information associated with the handheld surgical system operatively coupled to console 30'. Accordingly, console 30' may receive and optionally display information from handheld controller 300 such as the status of handheld controller 300 or the connected instrument and additionally raise errors through visual and auditory alarms.

Figure 15A:
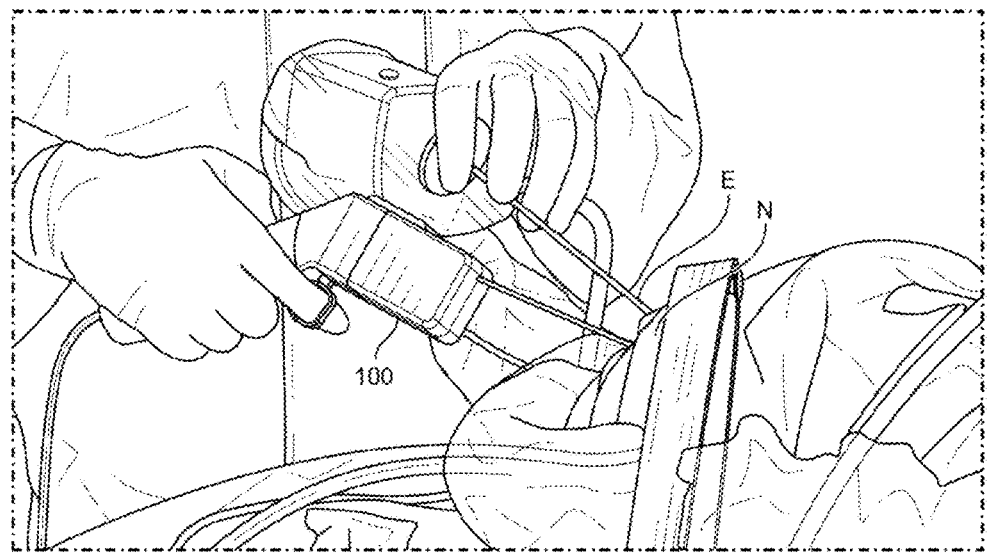
FIGS. 15A and 15B illustrate use of the handheld surgical system in an intranasal endoscopic procedure.
Figure 15B:
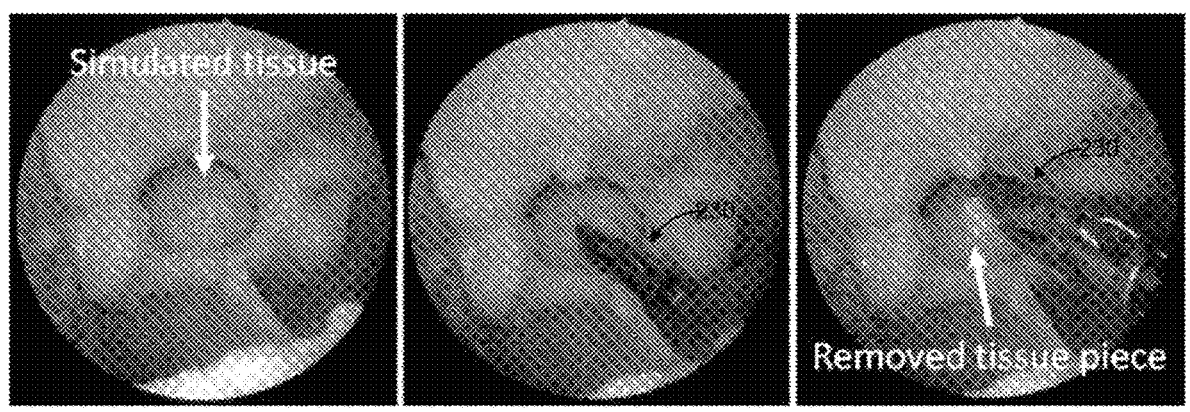

FIG. 15A illustrates handheld surgical system 100 in use through nose N with a commercially available endoscope E during a cadaveric trial replicating the endoscopic endonasal transsphenoidal approach for tumor removal from the pituitary gland located at the skull-base. FIG. 15B simulates the tissue removal technique inside a physical training model of the skull-base anatomy. Specifically, FIG. 15B demonstrates end-effector 230 (e.g., a grasper) of handheld surgical system 100 removing a piece of simulated soft tissue tumor inside a training model of the skull-base brain anatomy.

Figure 16A:
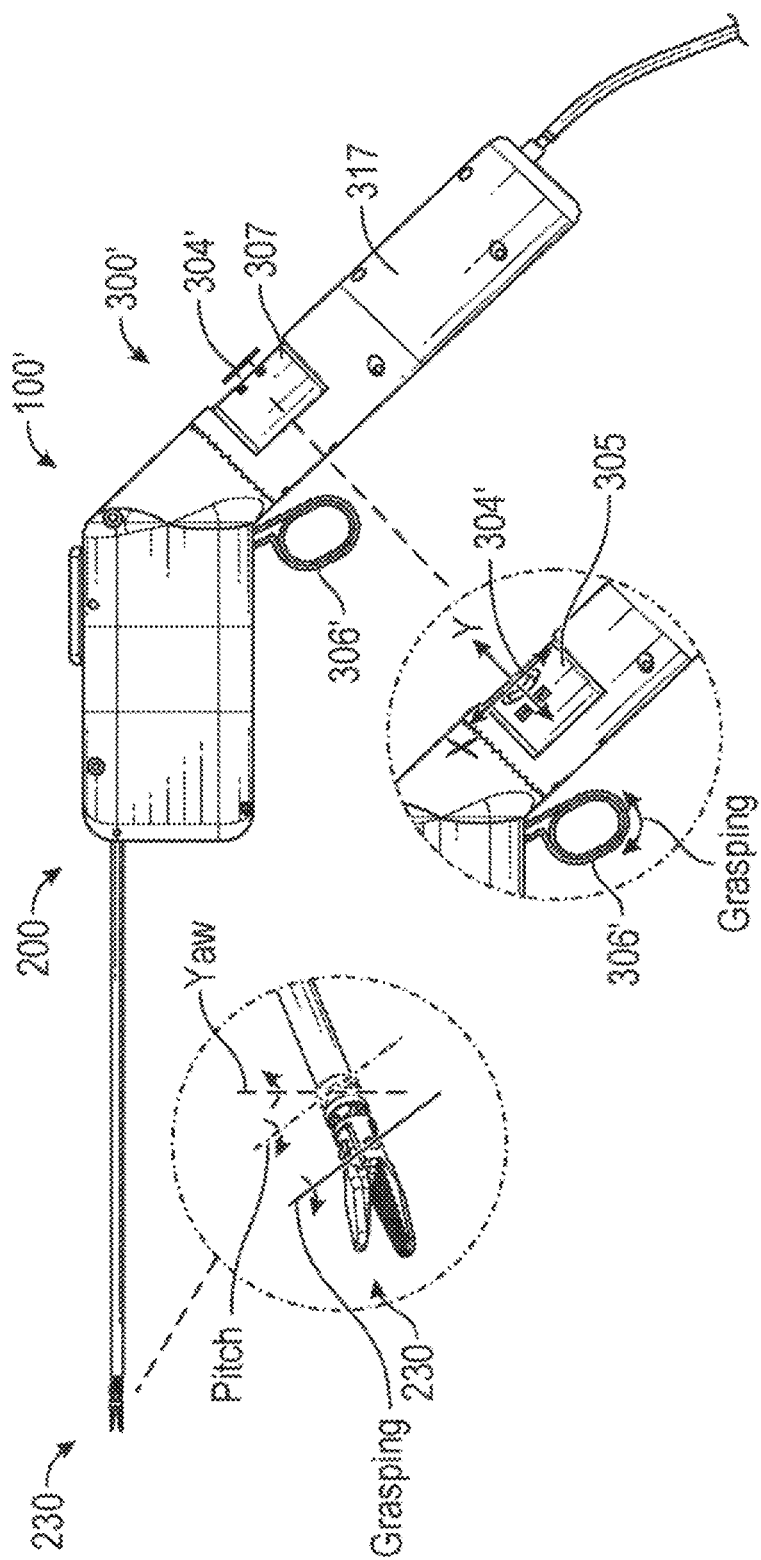
FIGS. 16A to 16D illustrate an alternative exemplary handheld surgical system constructed in accordance with the principles of the present disclosure.
Figure 16B:
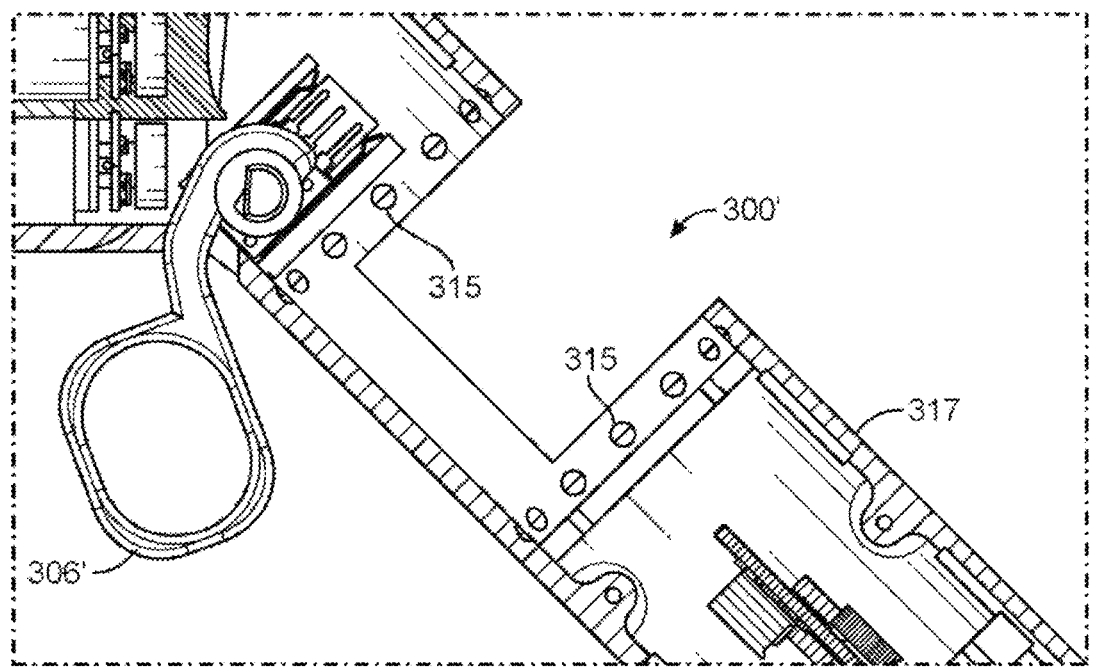
Figure 16C:
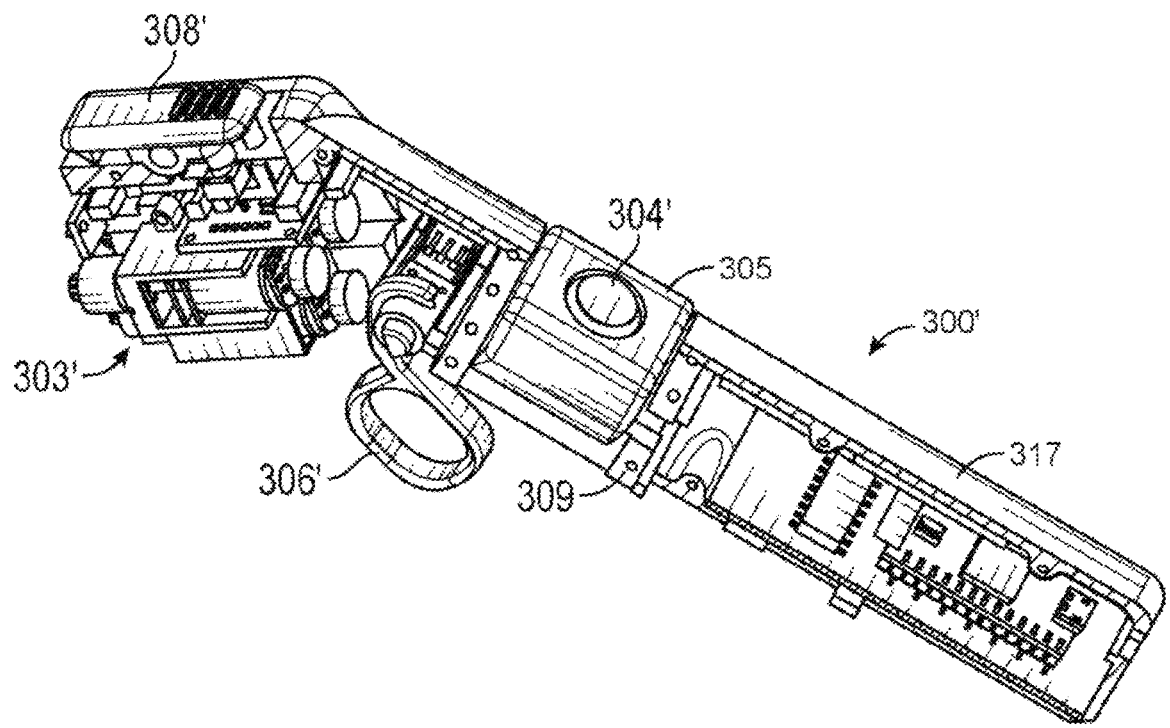
Figure 16D:
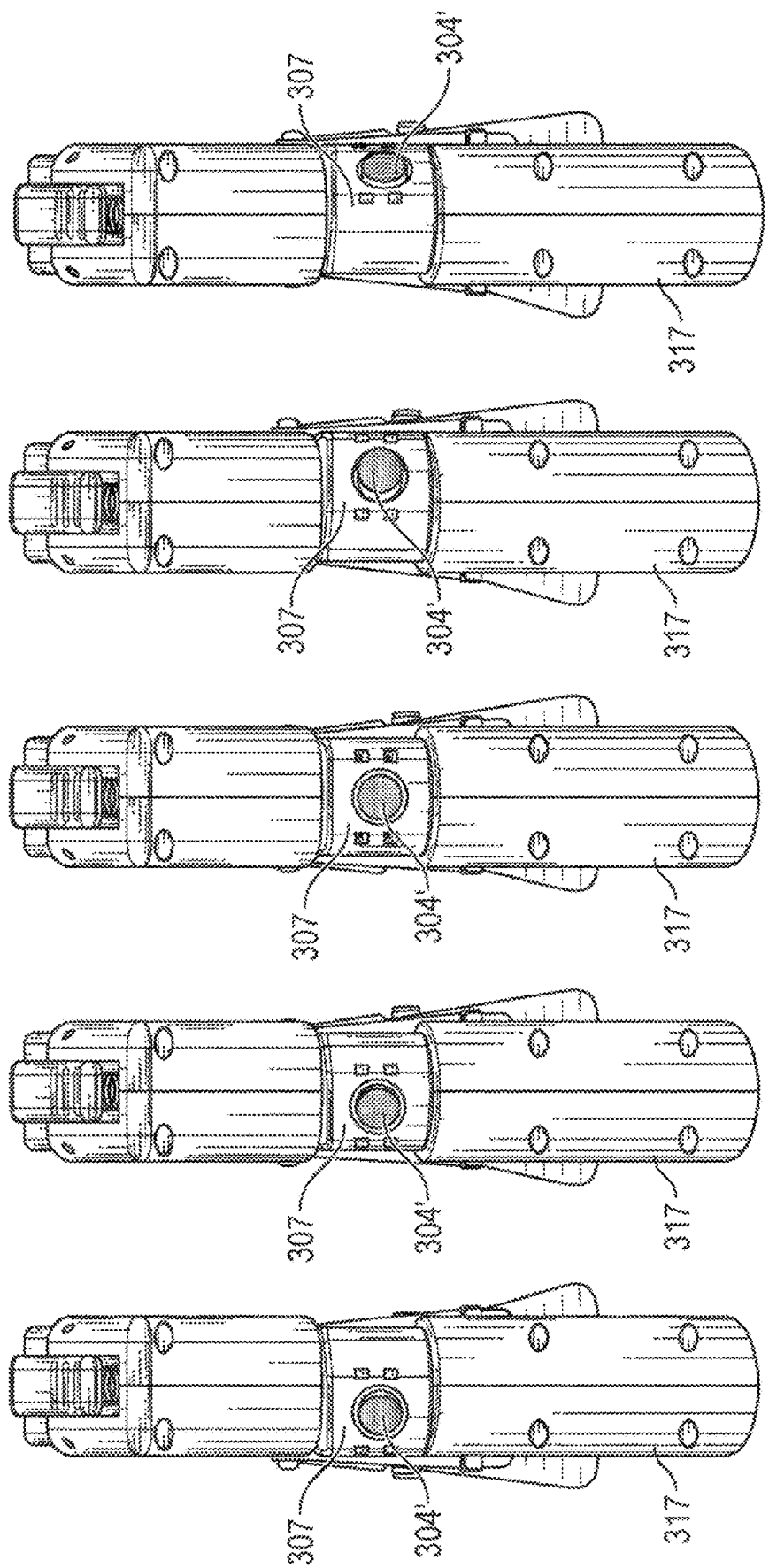

Referring now to FIGS. 16A to 16C, an alternative exemplary handheld surgical system is provided. Handheld surgical system 300' may be constructed similar to handheld surgical system 300, with similar components having like-prime reference numerals. For example, coupler interface 303', joystick 304', trigger 306', and latch 308' correspond with coupler interface 303, joystick 304, trigger 306, and latch 308. FIG. 16A illustrates the pitch, yaw, and grasping (open/close) axes around which the flexible instrument tip (e.g., end-effector 230) rotates, and the corresponding motions of joystick' and trigger 306'. Handheld surgical system 300' differs from handheld surgical system 300 in that the adjustable joystick may not be spring-loaded. For example, handle portion 317 may comprise movable joystick component 307 having joystick 304' disposed thereon. Moveable joystick component 307 is configured to be rotated relative to handle portion 317 to thereby selectively move the position of joystick 304' circumferentially along handle portion 317. As shown in FIGS. 16B and 16C, handle portion 317 may include a plurality of sockets 307 disposed circumferentially along the inner surface of handle portion 317, and moveable joystick component 307 may include a plurality of friction spheres 309 disposed circumferentially along the outer surface of moveable joystick component 307, such that friction spheres 309 are configured to releasably engage with sockets 307 at discrete angular positions. Accordingly, as shown in FIG. 16D, moveable joystick component 307, and accordingly joystick 304', may be selectively adjusted to ergonomically accommodate the preferences of different users.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed is:

1. A method for performing a surgical procedure, the method comprising:
providing a handheld controller comprising an interface operatively coupled to one or more motors;
providing an interchangeable instrument having a distal region comprising an end-effector, a proximal region comprising one or more capstan shafts, an elongated shaft extending between the proximal and distal regions, and one or more pairs of tendons, each pair of tendons having distal ends coupled to the end-effector and proximal ends extending through the elongated shaft towards a corresponding pair of capstans of the one or more capstan shafts via a pair of pulleys associated with the corresponding pair of capstans;

releasably coupling the handheld controller to the interchangeable instrument; and actuating the interface to cause at least one of the one or more motors to cause rotation of at least one of the one or more capstan shafts to thereby actuate the end-effector in one or more degrees of freedom, wherein rotation of each capstan shaft of the one or more capstan shafts in a first rotational direction causes a first tendon of the corresponding pair of tendons to move in a first axial direction and causes a second tendon of the corresponding pair of tendons to move in a second axial direction opposite the first axial direction to thereby actuate the end-effector in one of the one or more degrees of freedoms.

2. The method of claim 1, wherein the one or more capstan shafts comprise a first capstan shaft comprising a first pair of capstans operatively coupled to the end-effector via a first pair of tendons of the one or more pairs of tendons, and a second capstan shaft comprising a second pair of capstans operatively coupled to the end-effector via a second pair of tendons of the one or more pairs of tendons, and wherein actuating the interface comprises actuating the interface to cause a first motor of the one or more motors to cause rotation of the first capstan shaft to thereby actuate the end-effector in a pitch degree of freedom, and/or actuating the interface to cause a second motor of the one or more motors to cause rotation of the second capstan shaft to thereby actuate the end-effector in a yaw degree of freedom.

3. The method of claim 2, wherein distal ends of the first pair of tendons are coupled to opposite sides of the end-effector such that rotation of the first capstan shaft causes the first pair of tendons to cause rotation of the end-effector about a pitch axis, and wherein distal ends of the second pair of tendons are coupled to opposite sides of the end-effector such that rotation of the second capstan shaft causes the second pair of tendons to cause rotation of the end-effector about a yaw axis.

4. The method of claim 2, wherein the first and second capstan shafts are arranged in a linear configuration.

5. The method of claim 2, wherein the one or more capstan shafts comprise a third capstan shaft comprising a third pair of capstans operatively coupled to the end-effector via a third pair of tendons of the one or more pairs of tendons, the method further comprising actuating a second interface of the handheld controller to cause a third motor of the one or more motors to cause rotation of the third capstan shaft to thereby actuate the end-effector in an open and close degree of freedom.

6. The method of claim 5, wherein the second interface comprises a trigger.

7. The method of claim 5, wherein the end-effector comprises a jaw configured to rotate about a jaw axis perpendicular to a longitudinal axis of the end-effector, and wherein a first distal end of the third pair of tendons is coupled to a first side of the jaw and a second distal end of the third pair of tendons is coupled to an opposite side of the jaw, such that rotation of the third capstan shaft in the first rotational direction causes the third pair of tendons to rotate the jaw in a first direction about the jaw axis and rotation of the third capstan shaft in an opposite rotational direction causes the third pair of tendons to rotate the jaw in an opposite direction about the jaw axis.

8. The method of claim 5, wherein the first, second, and third capstan shafts are arranged in a triangular configuration.

9. The method of claim 1, wherein each capstan shaft of the one or more capstan shafts comprises an instrument coupler, wherein each motor of the one or more motors comprises a controller coupler, and wherein releasably coupling the handheld controller to the interchangeable instrument comprises operatively coupling each instrument coupler to a corresponding controller coupler of the one or more motors, such that the one or more motors cause rotation of the one or more capstan shafts via the corresponding instrument and controller couplers.

10. The method of claim 9, wherein the instrument coupler comprises a groove, wherein the controller coupler comprises a boss comprising a tapered portion configured to facilitate self-alignment of the controller coupler with the instrument coupler, and wherein operatively coupling each instrument coupler to the corresponding controller coupler comprises releasably engaging the boss with the groove to permit transmission of rotary motion from the one or more motors to the one or more capstan shafts.

11. The method of claim 10, wherein the one or more motors are disposed within a compliant motor pack, and wherein operatively coupling each instrument coupler to the corresponding controller coupler comprises applying a force to move the compliant motor pack within the handheld controller to facilitate self-alignment of the controller coupler with the instrument coupler.

12. The method of claim 1, wherein each capstan shaft of the one or more capstan shafts is configured to rotate about a respective capstan axis parallel to a longitudinal axis of the elongated shaft.

13. The method of claim 12, wherein each pair of pulleys associated with the one or more capstan shafts is configured to rotate about a respective pulley axis perpendicular to the longitudinal axis of the elongated shaft.

14. The method of claim 13, wherein the respective pulley axis is angled to align the corresponding pair of pulleys in a direction towards the pair of capstans of the associated one or more capstan shafts.

15. The method of claim 13, wherein each pair of pulleys associated with the one or more capstan shafts is aligned with the longitudinal axis of the elongated shaft to thereby route the one or more pairs of tendons from the one or more capstan shafts through the elongated shaft.

16. The method of claim 13, wherein a first pair of pulleys associated with a first capstan shaft of the one or more capstan shafts is configured to rotate about a first pulley axis, and wherein a second pair of pulleys associated with a second capstan shaft of the one or more capstan shafts is configured to rotate about a second pulley axis offset from the first pulley axis.

17. The method of claim 1, wherein a distal end of the elongated shaft comprises a ball joint base pivotally engaged with a ball at a proximal end of the end-effector to form a ball joint, and wherein actuating the interface causes movement of the end-effector in at least one of two degrees of freedom about the ball joint.

18. The method of claim 1, wherein rotation of each capstan shaft of the one or more capstan shafts in a second rotational direction opposite the first rotational direction causes the first tendon of the corresponding pair of tendons to move in the second axial direction and causes the second tendon of the corresponding pair of tendons to move in the first axial direction to thereby actuate the end-effector in the one of the one or more degrees of freedoms.

19. The method of claim 1, further comprising actuating a latch to transition the latch from an unlocked state to a locked state to lock the handheld controller to the interchangeable instrument.

20. The method of claim 1, further comprising measuring an angular position of each capstan shaft of the one or more capstan shafts via one or more sensors of the interchangeable instrument, the angular position of each capstan shaft indicative of an amount of actuation of the end-effector in each of the one or more degrees of freedoms.

21. The method of claim 1, wherein the interface comprises a joystick.

22. The method of claim 1, wherein the handheld controller comprises a connection portion configured to be removably coupled to the interchangeable instrument, and a handle portion rotatably coupled to the connection portion, the handle portion sized and shaped to be held in a user's palm and comprising the interface, the method further comprising:
    selectively rotating the handle portion relative to the connection portion at predefined increments to ergonomically align the interface with the user's thumb.

23. The method of claim 22, wherein selectively rotating the handle portion relative to the connection portion comprises:
    pulling the handle portion away from the connection portion;
    rotating the handle portion relative to the connection portion via a hirth joint; and
    releasing the handle portion, such that a compression spring coupling the handle portion to the connection portion biases the handle portion towards the connection portion to thereby maintain a position of the handle portion relative to the connection portion.

24. The method of claim 1, further comprising actuating a second interface to cause the end-effector to return to a linear configuration.

25. The method of claim 1, further comprising:
    selecting the interchangeable instrument from a plurality of interchangeable instruments based on the surgical procedure, each of the plurality of interchangeable instruments comprising a long grasper, a short grasper, a ring-curette, a long ring-curette, a spoon curette, a suction tip, an endoscope, a needle holder, a scissor, or a dissector,
    wherein releasably coupling the handheld controller to the interchangeable instrument comprises releasably coupling the handheld controller to the selected interchangeable instrument.

26. The method of claim 1, further comprising applying a drape between the interchangeable instrument and the handheld controller to maintain sterility of the handheld controller during the surgical procedure.

27. The method of claim 1, further comprising providing power to the handheld controller via a console operatively coupled to the handheld controller.

28. The method of claim 1, wherein actuating the interface to actuate the end-effector comprises actuating the interface to cause the end-effector to move in the one or more degrees of freedom to perform minimally invasive neurosurgery.

29. The method of claim 28, further comprising visualizing an operative workspace of the end-effector via a neuroendoscope.

30. The method of claim 28, wherein the elongated shaft is sized and shaped to be inserted through a nasal passageway, the method further comprising:
    inserting the distal region of the interchangeable instrument through the nasal passageway of a patient,
    wherein actuating the interface to actuate the end-effector comprises actuating the interface to cause the end-effector to move in the one or more degrees of freedom to perform the minimally invasive neurosurgery on a brain of the patient.

* * * * *